(12) United States Patent
Kobayashi

(10) Patent No.: US 8,040,514 B2
(45) Date of Patent: Oct. 18, 2011

(54) DENTAL COLOR MEASUREMENT TOOL, DENTAL COLOR MEASUREMENT TOOL SYSTEM, AND DENTAL COLOR MEASUREMENT SYSTEM

(75) Inventor: Hiroyoshi Kobayashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 396 days.

(21) Appl. No.: 12/341,138

(22) Filed: Dec. 22, 2008

(65) Prior Publication Data

US 2009/0168063 A1    Jul. 2, 2009

(30) Foreign Application Priority Data

Dec. 28, 2007    (JP) .................................. 2007-340316

(51) Int. Cl.
*G01J 3/46*    (2006.01)
*A61C 19/10*    (2006.01)
(52) U.S. Cl. ............ 356/402; 356/244; 396/16; 433/26; 433/29; 433/215
(58) Field of Classification Search .................. 356/402; 433/26, 29, 215; 396/14, 16
See application file for complete search history.

(56) References Cited

U.S. PATENT DOCUMENTS 6,540,513 B2    4/2003 Berner et al.

FOREIGN PATENT DOCUMENTS

JP    2007-167142 A    7/2007

*Primary Examiner* — F. L. Evans
(74) *Attorney, Agent, or Firm* — Holtz, Holtz, Goodman & Chick, P.C.

(57) ABSTRACT

A dental color measurement tool disposed opposite an opening portion for capturing light from an artificial tooth to undergo color measurement with a color measurement device includes at least one pair of guide posts having an engaging portion corresponding to an engaging portion on the color measurement device side, and an abutment post disposed between the pair of guide posts and having a pointed convex shape to which the artificial tooth can be mounted. The abutment post has a color measurement reference surface in a color measurement light axis direction as the vicinity of a focus position of the color measurement device in a photographing state. When performing color measurement photographing, the artificial tooth is mounted to the abutment post to position the front thereof at the color measurement reference surface. Thus, the artificial tooth can be stably retained at a suitable position with respect to the color measurement device.

15 Claims, 22 Drawing Sheets

US 8,040,514 B2

DENTAL COLOR MEASUREMENT TOOL, DENTAL COLOR MEASUREMENT TOOL SYSTEM, AND DENTAL COLOR MEASUREMENT SYSTEM

CROSS REFERENCE TO RELATED APPLICATION

This application claims benefit of Japanese Application No. 2007-340316 filed in Japan on Dec. 28, 2007, the contents of which are incorporated by this reference.

BACKGROUND OF THE INVENTION

1. Field of the Invention

The present invention relates to a dental color measurement tool in which an artificial tooth is mounted when measuring the color of the artificial tooth using a color measurement device, a dental color measurement tool system including the dental color measurement tool and a dark box, and a dental color measurement system including a color measurement device.

2. Description of the Related Art

Conventionally, there are cases in which photographing (color measurement photographing) is performed for color measurement using a dental color measurement device (color measuring camera) in order to check the color shade of an artificial tooth that is manufactured at a dental laboratory. In such cases, photographing is performed in a state in which the artificial tooth as the object of measurement is positioned in an opening portion of a photographing window of the color measurement device at the time of photographing.

For example, an artificial tooth mounting stand disclosed in Patent Document 1 can be applied as a device that positions the aforementioned artificial tooth at an opening portion of a photographing window of the aforementioned color measurement device at the time of photographing.

FIG. 38 is a view that illustrates a state in which color measurement (photographing) of an artificial tooth 203a is performed using an artificial tooth mounting stand 203 by a color measuring camera 201 according to a method for measuring the color of an artificial tooth that is disclosed in U.S. Pat. No. 6,540,513. The artificial tooth mounting stand 203 on which the artificial tooth 203a is mounted is fixedly supported on a support pedestal 202 by a magnet 205, and the support pedestal 202 is adhered to a table 206 by a magnet 204. The color measuring camera 201 is held at a position to the front of the artificial tooth 203a by a photographer, and photographing is performed.

SUMMARY OF THE INVENTION

A dental color measurement tool according to the present invention stably holds an artificial tooth at a suitable position with respect to a color measurement device. The dental color measurement tool of the present invention is disposed opposite an opening portion for capturing a light from an artificial tooth that is to undergo color measurement with a color measurement device, and includes: at least one pair of guide posts having an engaging portion corresponding to an engaging portion on the color measurement device side; and an abutment post that is disposed between the one pair of guide posts and that has a shape that enables mounting of the artificial tooth, and which is also provided with a color measurement reference surface in a direction of a color measurement light axis of the color measurement device.

A dental color measurement tool system of the present invention includes a dental color measurement tool and a dark box that houses the dental color measurement tool to block out extraneous light in a state of performing color measurement photographing of the artificial tooth that is mounted in the dental color measurement tool.

A dental color measurement system of the present invention includes a dental color measurement tool, a dark box that houses the dental color measurement tool to block out extraneous light in a state of performing color measurement photographing of an artificial tooth that is mounted in the dental color measurement tool, and the color measurement device for performing color measurement of the artificial tooth that is mounted in the dental color measurement tool.

Other features and advantages of the present invention will be apparent from the following description.

DETAILED DESCRIPTION OF THE PREFERRED EMBODIMENTS

Hereunder, embodiments of the present invention are described with reference to the drawings.

Figure 1:
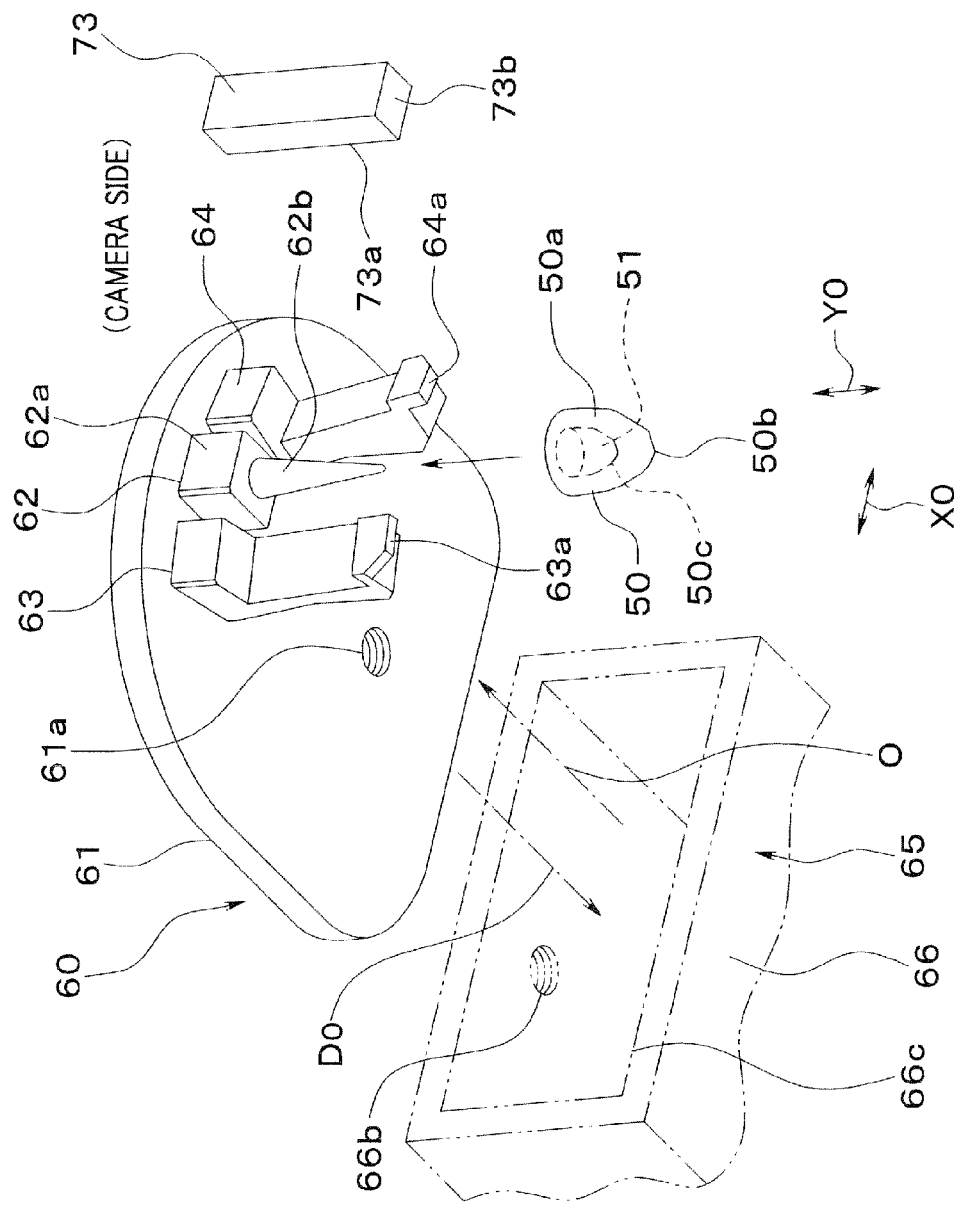
FIG. 1 is an exploded perspective view of a dental color measurement tool and a dark box for color measurement (only one portion of the main body of the dark box is shown) that constitute a dental color measurement tool system of a first embodiment of the present invention.
Figure 2:
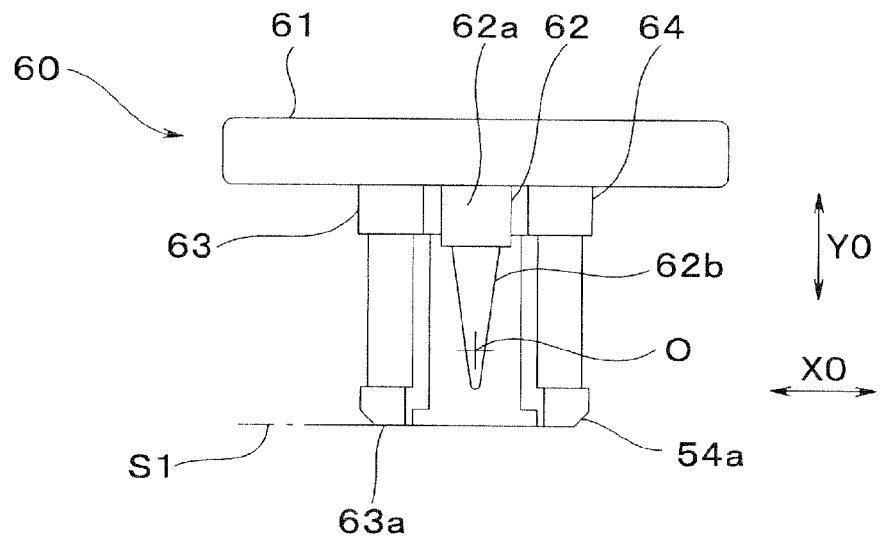
FIG. 2 is a front view of the dental color measurement tool shown in FIG. 1 (as seen from the direction of the color measurement light axis)
Figure 3:
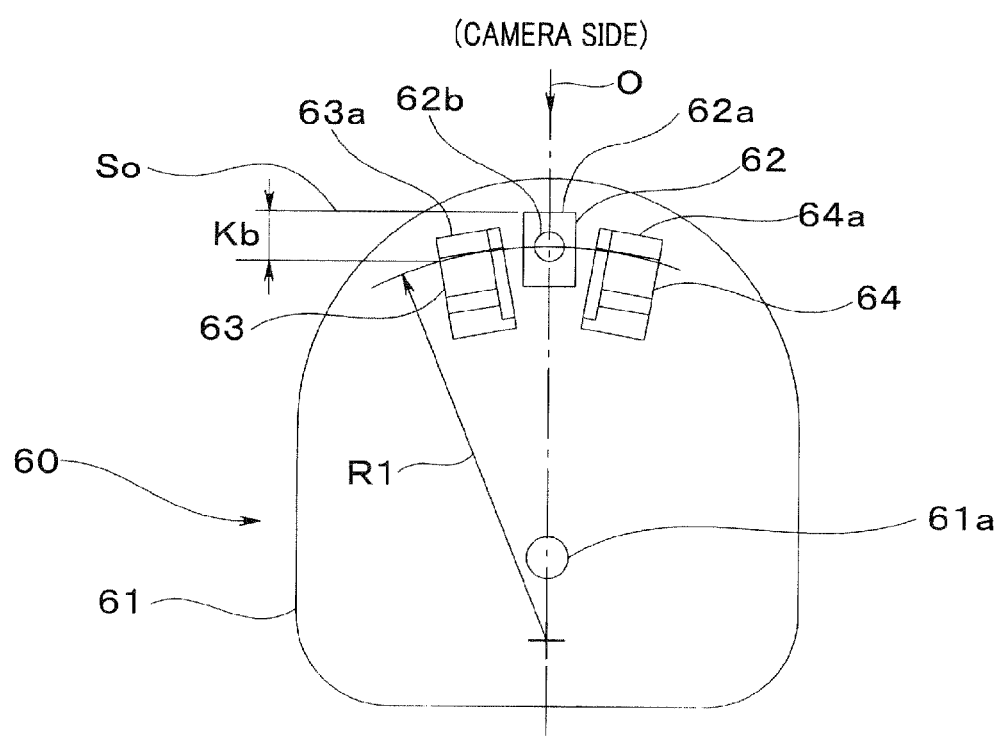
FIG. 3 is a bottom view of FIG. 2.
Figure 4:
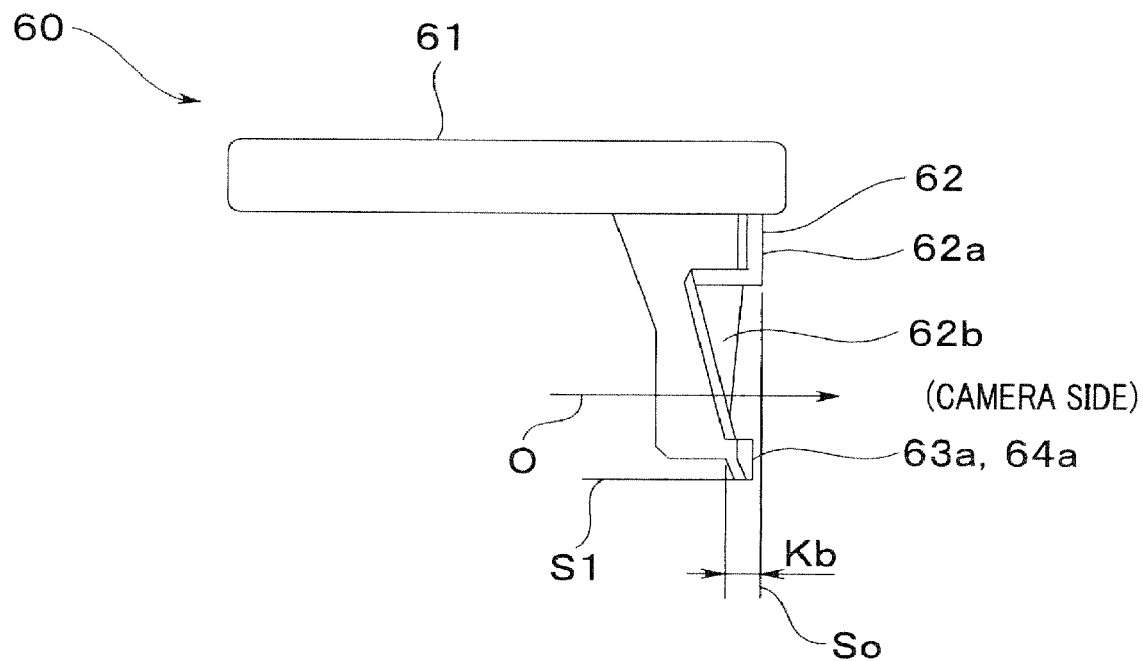
FIG. 4 is a side view of FIG. 2.
Figure 5:
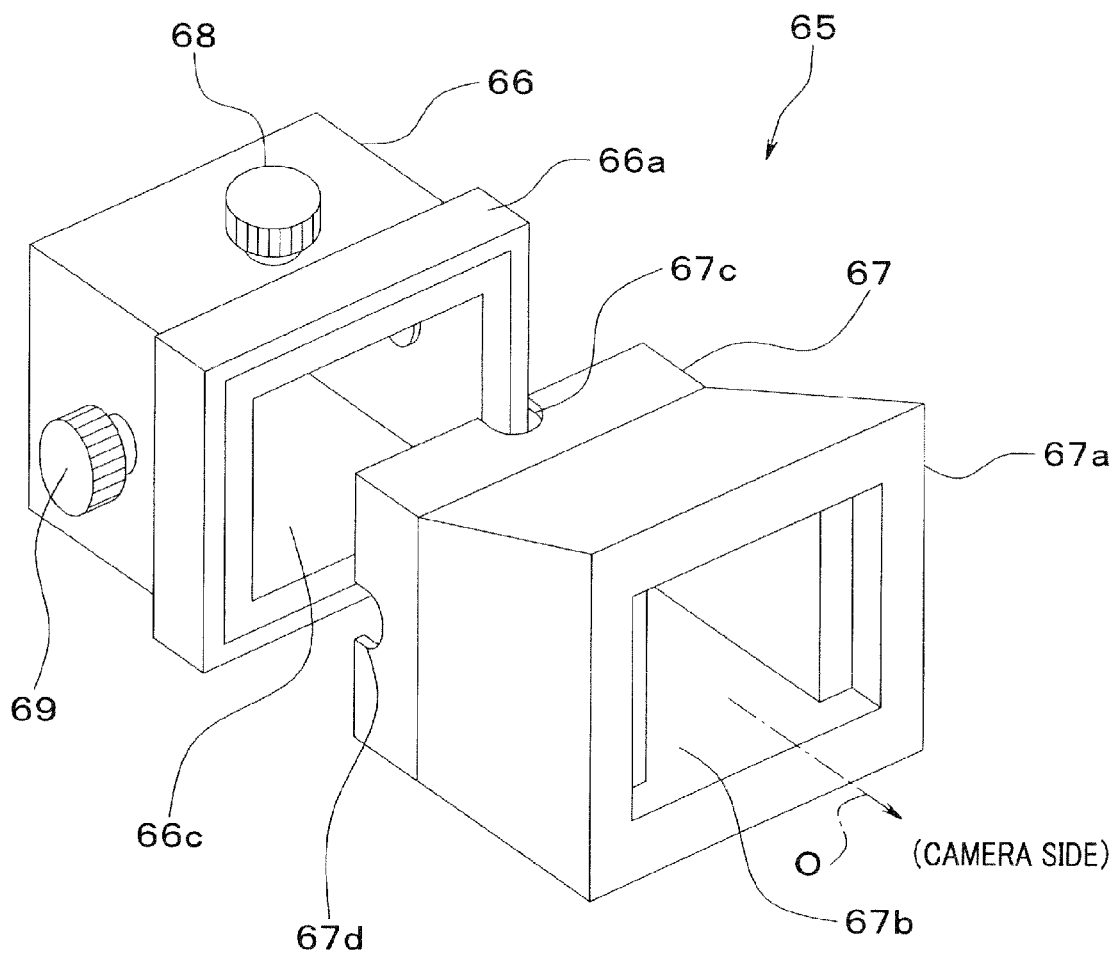
FIG. 5 is an exploded perspective view of the dark box shown in FIG. 1.
Figure 6:
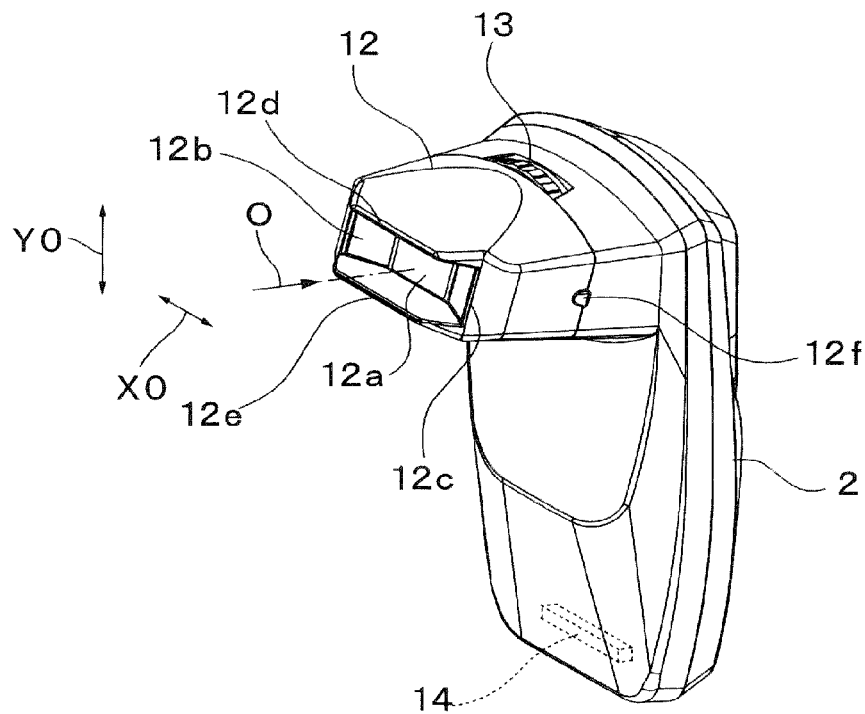
FIG. 6 is a perspective view of a camera of a dental color measurement device included in a dental color measurement system for performing color measurement of an artificial tooth using the dental color measurement tool system shown in FIG. 1.
Figure 7:
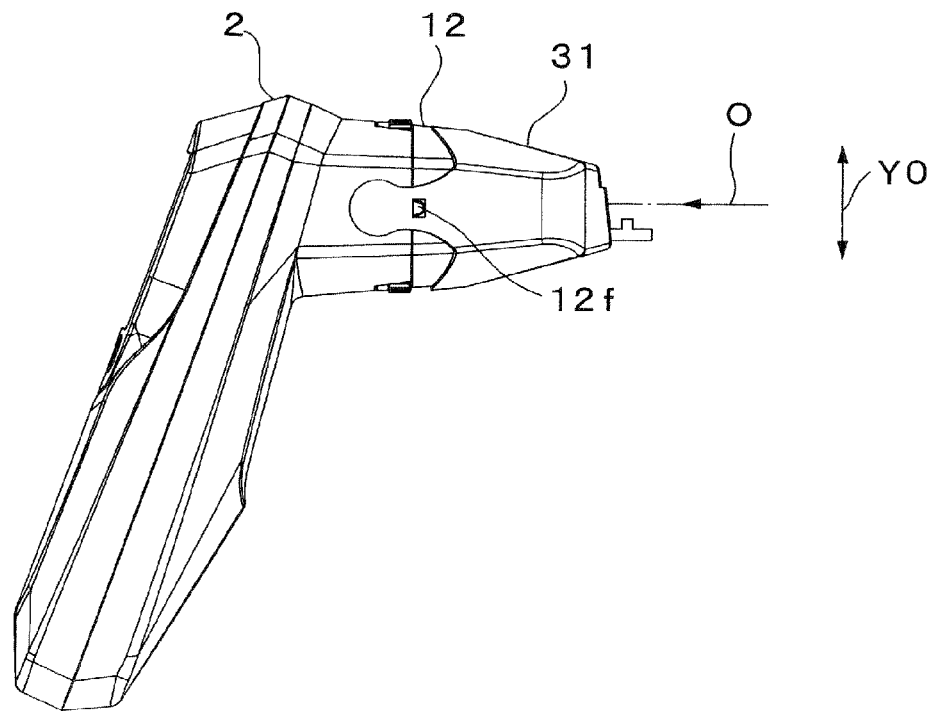
FIG. 7 is a side view of a state in which the camera shown in FIG. 6 is covered with a contact cap for tooth measurement.
Figure 8:
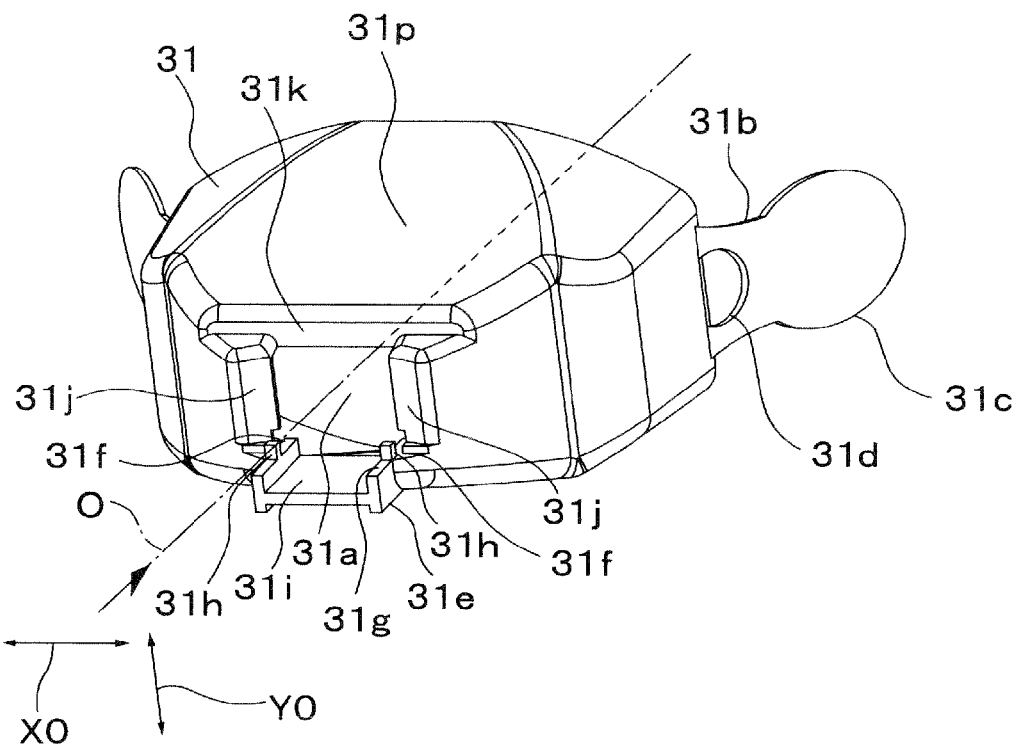
FIG. 8 is a perspective view of the contact cap shown in FIG. 7.
Figure 9:
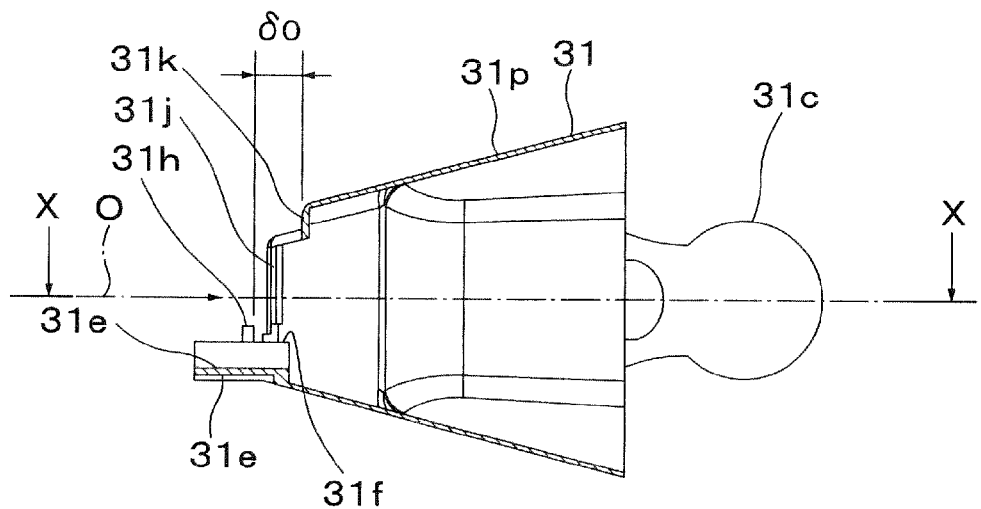
FIG. 9 is a longitudinal sectional view along a color measurement light axis of the contact cap shown in FIG. 7.
Figure 10:
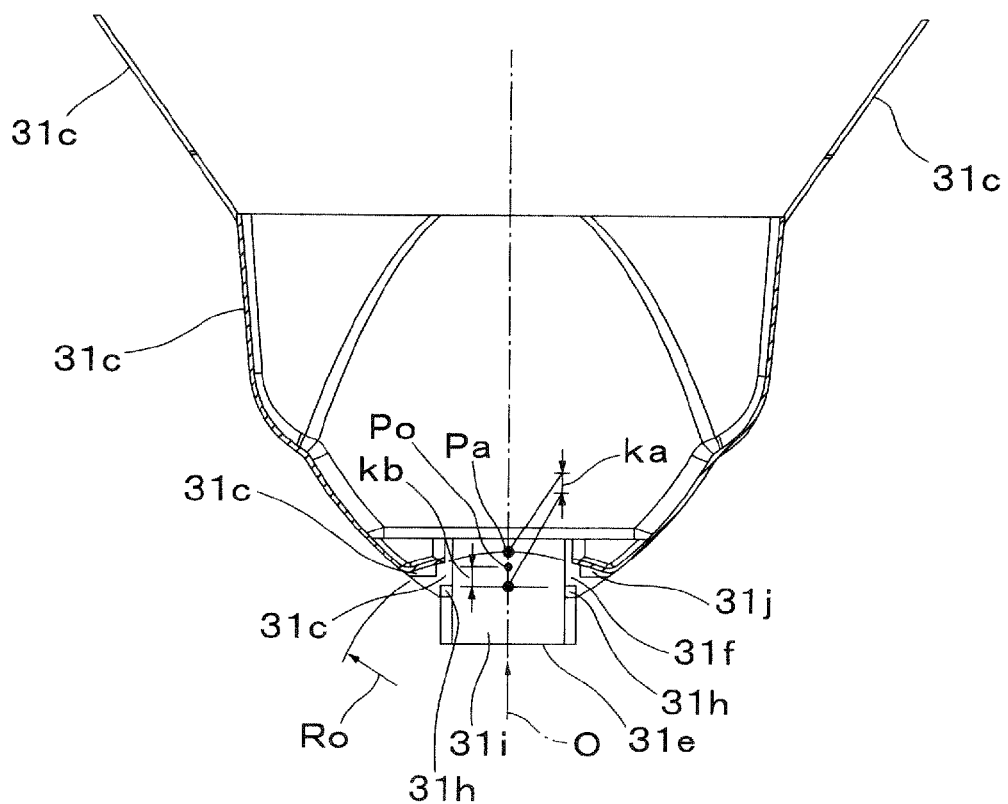
FIG. 10 is a sectional view along a line X-X in FIG. 9.
Figure 11:
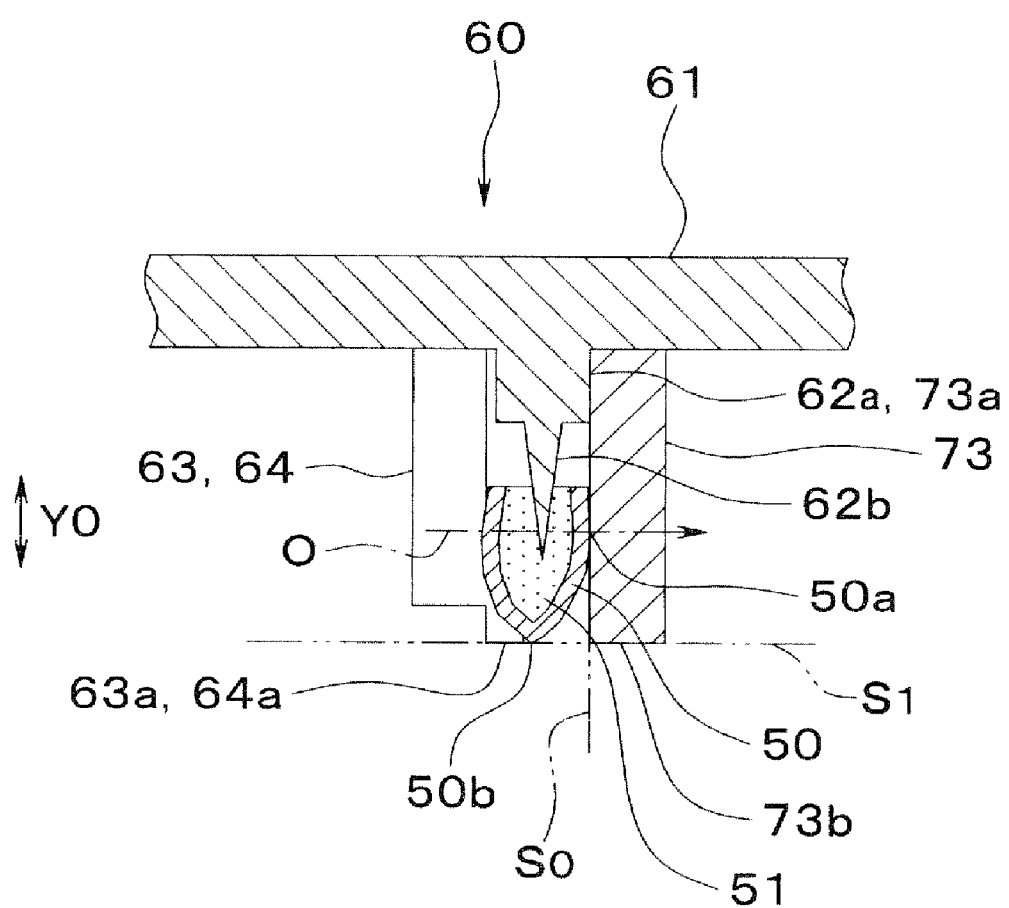
FIG. 11 is a sectional view along the color measurement light axis that illustrates an artificial tooth positional adjustment state in which an artificial tooth is mounted to the dental color measurement tool shown in FIG. 1.
Figure 12:
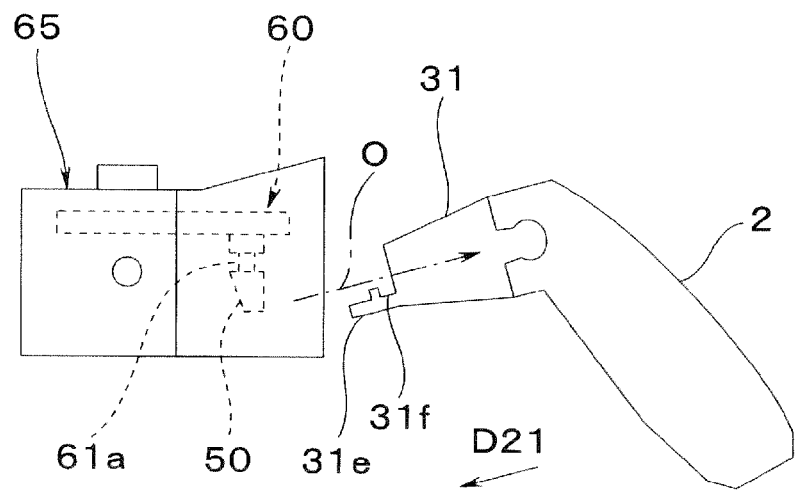
FIG. 12 is a side view showing a state immediately prior to fitting a distal end portion of the camera of the aforementioned dental color measurement device into the aforementioned dental color measurement tool after mounting of the dental color measurement tool in the artificial tooth mounting state shown in FIG. 11 to the dark box.
Figure 13:
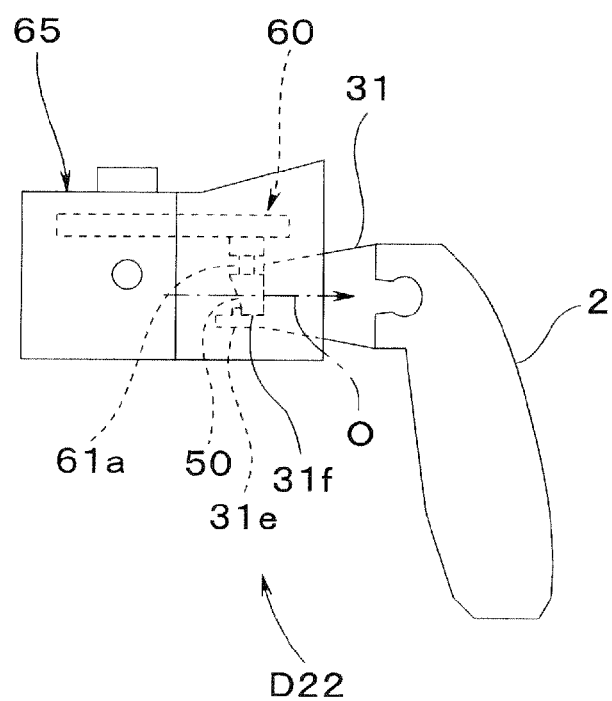
FIG. 13 is a side view of a state in which the aforementioned distal end portion of the camera has been fitted into the dental color measurement tool (state in which color measurement photographing is possible)
Figure 14:
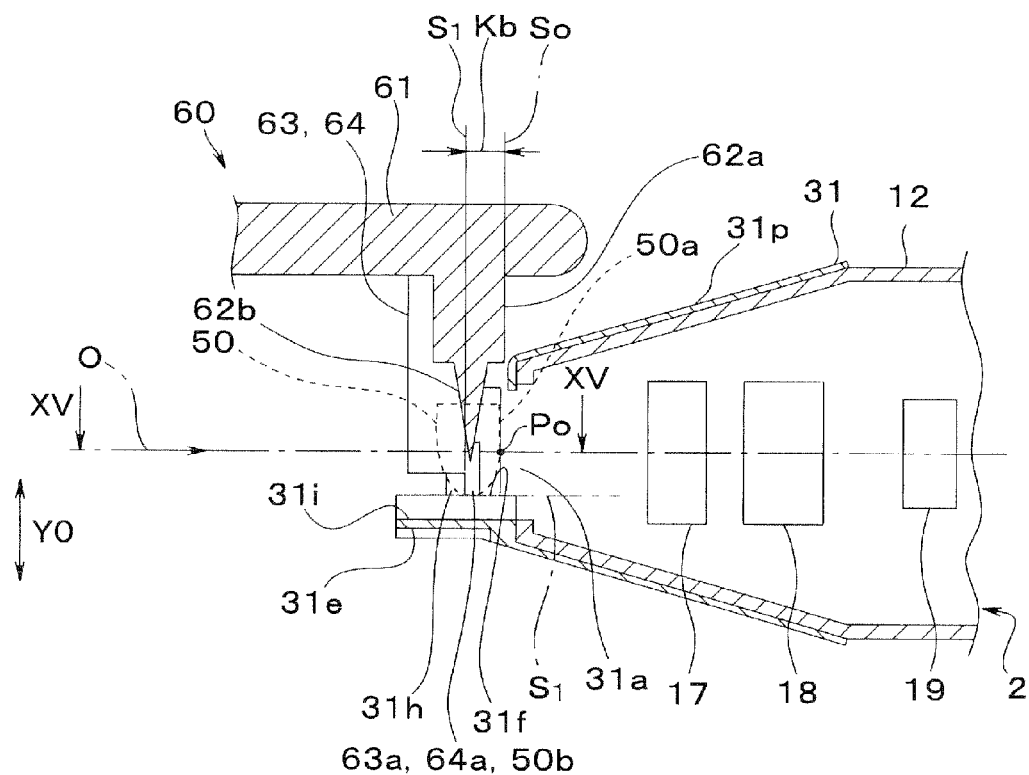
FIG. 14 is an enlarged sectional view of a state in which the aforementioned distal end portion of the camera is fitted into the dental color measurement tool (state in which color measurement photographing is possible)
Figure 15:
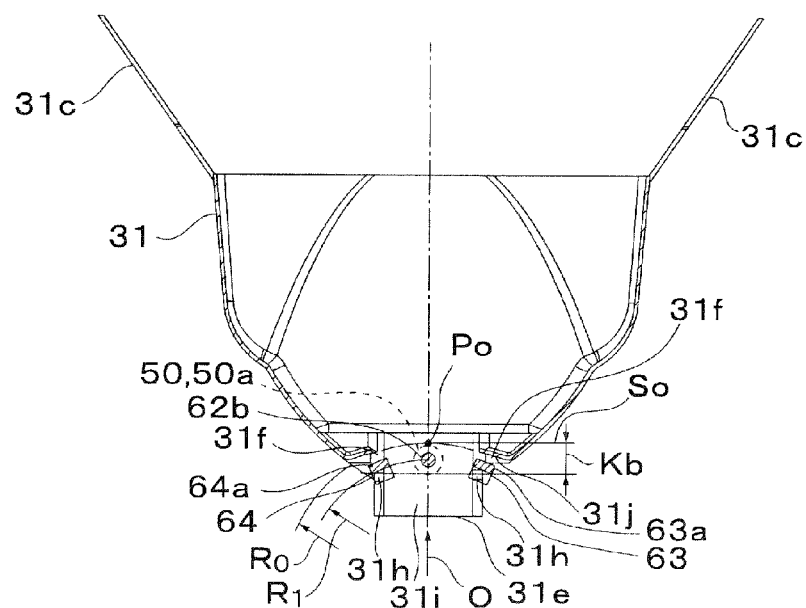
FIG. 15 is a sectional view along line XV-XV shown in FIG. 14, and illustrates a state in which the aforementioned contact cap is fitted into the aforementioned dental color measurement tool.

FIG. 1 is an exploded perspective view of a dental color measurement tool and a dark box for color measurement (only one portion of the main body of the dark box is shown) that constitute a dental color measurement tool system of the first embodiment of the present invention. FIG. 2 is a front view of the dental color measurement tool shown in FIG. 1 (view from the direction of the color measurement light axis). FIG. 3 is a bottom view of FIG. 2. FIG. 4 is a side view of FIG. 2. FIG. 5 is an exploded perspective view of the aforementioned dark box. FIG. 6 is a perspective view of a camera of a dental color measurement device included in a dental color measurement system for performing color measurement of an artificial tooth using the dental color measurement tool system shown in FIG. 1. FIG. 7 is a side view of a state in which the aforementioned camera is covered with a contact cap for tooth measurement. FIG. 8 is a perspective view of the contact cap shown in FIG. 7. FIG. 9 is a longitudinal sectional view along the color measurement light axis of the contact cap shown in FIG. 7. FIG. 10 is a sectional view along line X-X in FIG. 9. FIG. 11 is a sectional view along the color measurement light axis that illustrates an artificial tooth positional adjustment state in which an artificial tooth is mounted in the dental color measurement tool shown in FIG. 1. FIG. 12 is a side view showing a state immediately prior to fitting a distal end portion of the camera of the aforementioned dental color measurement device into the aforementioned dental color measurement tool after mounting of the dental color measurement tool in the artificial tooth mounting state shown in FIG. 11 to the dark box. FIG. 13 is a side view of a state in which the distal end portion of the camera has been fitted into the dental color measurement tool (state in which color measurement photographing is possible). FIG. 14 is an enlarged sectional view of a state in which the camera distal end portion is fitted into the dental color measurement tool (state in which color measurement photographing is possible). FIG. 15 is a sectional view along line XV-XV shown in FIG. 14 that illustrates a state in which the contact cap is fitted into the dental color measurement tool.

A dental color measurement tool system according to the present embodiment includes a color measurement tool 60 (FIGS. 1 and 2) as a dental color measurement tool, a dark box 65 for color measurement (FIG. 5) that houses the color measurement tool, and a reference plate 73. In this case the color measurement tool 60 is configured to be insertable into the dark box 65 in a state in which an artificial tooth 50 that was produced at a dental laboratory is mounted therein. The color of the surface of the artificial tooth 50 is photographed by a camera 2 (FIG. 6) as a dental color measurement device in a state in which the color measurement tool 60 has been inserted into the dark box 65. Photograph data for the artificial tooth that is outputted from the camera 2 is used for calculating color measurement data for the artificial tooth 50. By calculating this color measurement data, the exact color of the artificial tooth 50 is measured.

The artificial tooth 50 is a so-called crown-shaped implant of a type in which a ceramic layer is formed on the surface of a metal crown or is an all-ceramic crown that does not use a metal crown is applied. The artificial tooth 50 is covered over an abutment of a vital tooth formed by medical treatment (particularly for front teeth) or over a metallic abutment and adhered thereto.

As shown in FIGS. 12, 13, and 14, the artificial tooth 50 is mounted to the color measurement tool 60, the color measurement tool 60 is housed in the dark box 65 in order to block out extraneous light, and the artificial tooth 50 is positioned with respect to the camera 2 on which the contact cap 31 has been mounted. After positioning, the surface of the artificial tooth 50 is photographed by the camera 2, color measurement data is obtained from the photographed image, and the color shade of the artificial tooth 50 is determined.

The configuration of the color measurement tool 60 and the dark box 65 as well as the method of mounting the artificial tooth 50 are described in detail later. First, the camera 2 is described.

The camera 2 is a photographing device that together with a cradle (not shown) configures a HMSC device (Handy Multi-Spectral Camera) that is a dental tooth measurement (photographing) device, and the details thereof are described in Japanese Patent Application Laid-Open Publication No. 2007-167142.

In the above-described HMSC device, after mounting the camera 2 in the aforementioned cradle and charging the battery thereof, the camera 2 is removed from the cradle and, with the contact cap 31 (FIG. 8) in an attached state, color measurement photographing is performed to measure the color of a vital tooth or an artificial tooth or the like that is mounted in the color measurement tool 60. After photographing, the camera 2 is again mounted in the cradle and the photographed image data is transferred to a personal computer side via a USB. Various kinds of image processing are executed at the personal computer to determine the color shade of the surface of the vital tooth or artificial tooth.

As shown in FIGS. 6 and 14, the camera 2 includes, on the inside of a top cover 12 of the main body of the camera 2, an LED illumination system 17 including a plurality of LEDs, a photographing optical system 18 that is capable of focusing and that has a photographing optical axis, i.e. a color measurement light axis (hereunder, referred to as "optical axis O"), and an image pickup portion 19 that includes a built-in color CCD.

In the following description, the object to be measured side (side of the tooth or artificial tooth to be measured) in the optical axis O direction of the contact cap (described later) and the camera is taken as the front, and the image pickup portion side (camera side) is taken as the rear. The front-to-rear direction of the color measurement tool that is mounted to the contact cap and camera is described as the "camera side" (rearward side of the camera), and the side opposite thereto is described as the "side opposite the camera" (frontward side of the camera). Further, in the drawings, the longitudinal direction (vertical direction) of the abutment post 62, described later, which is a direction that is orthogonal to the optical axis O of the contact cap 31 and the camera 2 is referred to as the "Y0 direction", and a direction (horizontal direction) that is orthogonal to both the optical axis O and the Y0 direction is referred to as the "X0 direction". The same description also applies to the other embodiments.

As shown in FIG. 6, the top cover 12 is provided with a photographing window portion 12a as an opening portion in the front center thereof and illumination window portions 12b that are arranged on both sides of the photographing window portion 12a. A latching protrusion 12f for latching the contact cap 31 is arranged at both side ends at the rear of the top cover 12. A focus ring 13 for focus position adjustment is arranged on the top portion. The contact cap 31 for positioning a tooth to be measured, for example, a vital tooth or an artificial tooth 50, and blocking out extraneous light when executing color measurement photographing is mounted in the state shown in FIG. 7 on the outside of the top cover 12.

The contact cap 31 is a member having the shape of a thin-walled cap that is made from a material such as black elastic synthetic resin rubber, for example, styrene elastomer, and is covered over the front of the top cover 12 of the camera 2 and used (FIG. 7).

As shown in FIGS. 8 and 9, the contact cap 31 is provided with a cap portion 31p that is attached to cover the top cover 12 at the front, a central opening portion 31a as a photographing window portion to be disposed at a central position on the optical axis O in front of the photographing optical system 18 in an attached state at the front side of the cap portion, a front upper side portion 31k which forms the upper side of the opening portion 31a, a bite portion 31e as a protrusion portion to be disposed in a protruding state in the direction of the optical axis O below the opening portion 31a, flexible membranous wall portions 31j forming the left and right sides of the opening portion 31a, and two extending portions 31b that extend backward to the left and the right of the cap portion 31p in parallel with the direction of the optical axis O.

The inside surface of the cap portion 31p is provided as a satin-finished surface to prevent reflection. The shape of the inside surface of the cap portion 31p is vertically and horizontally symmetrical and can be attached to the top cover 12 even when the cap portion 31p is upside down.

The size of the central opening portion 31a of the contact cap 31 is about 16 mm with respect to the left to right width and about 14 mm with respect to the vertical length (this represents the length as far as an upper side portion 31f of the bite portion; the length as far as a concave portion 31i of the bite portion is 16 mm). This size partially includes teeth adjacent to the tooth to be measured that is the photographing object, assuming that the tooth to be measured is, for example, an incisor tooth (including the artificial tooth 50) of a normal adult that has an upper limit of approximately a 10 mm square.

The bite portion 31e of the contact cap 31 is disposed below the opening portion 31a and has a channel shape (groove shape) or a U-shaped cross sectional shape which protrudes towards the front in parallel with the optical axis O. The bite portion 31e includes the concave portion 31i, right and left upper side portions 31f as biting portions rising from the concave portion 31i that form the right and left channel upper sides, and right and left upper side portions 31g as portions that extend forward. The bite portion 31e also includes columnar convex portions 31h as positioning portions (engaging portions) to be disposed on the right and left sides of the upper side portions 31f in order to position a tooth to be measured (including the artificial tooth 50) in the optical axis O direction.

Wall portions 31j of the contact cap 31 are arranged on a cylindrical inner peripheral surface of a radius R0 that is centered on the optical axis O. The aforementioned radius R0 is set based on the arrangement of teeth around an incisor tooth of a common patient. If a distance between the rear end face of the columnar convex portions 31h and a point of intersection Pa with the optical axis O on the aforementioned cylindrical inner peripheral surface is taken as Ka, a best focus position P0 of the photographing optical system 18 of the camera 2 is located at the front side in the vicinity the point of intersection Pa, and a distance between the best focus position P0 and a rear end face (camera side) of the columnar convex portions 31h is taken as Kb, then Kb<Ka (FIG. 10).

When a tooth to be measured is an incisor tooth, positioning of the tooth to be measured is carried out by the incisor tooth biting the bite portion 31e. More specifically, at the time of photographing, a lower tooth that is on the side opposite to the incisor tooth contacts against the bottom surface of the bite portion 31e, and at the same time the teeth adjacent to the incisor tooth on both sides thereof are inserted from the upper side at the rear side (front side as viewed from the patient's side) of the columnar convex portions 31h, and the upper side portion 31f is lightly bitten as the inner surfaces of the adjacent teeth contact against the rear of the columnar convex portions 31h. In this biting state, the incisor tooth that is at the central part of the opening portion 31a undergoes positioning in the direction of the optical axis O, and is thereby positioned in the vicinity of the best focus position (the best focus position deviates somewhat according to differences in teeth shapes) of the photographing optical system 18 of the camera 2.

When the tooth to be measured is the artificial tooth 50, the artificial tooth 50 is held via the color measurement tool 60, and photographing can be performed after positioning the front surface (camera side) of the artificial tooth 50 in the vicinity of the best focus position P0 by positioning the artificial tooth 50. The method of positioning is described later. In this connection, the other dimensions of the contact cap 31 are described in the aforementioned Japanese Patent Application Laid-Open Publication No. 2007-167142.

The color measurement tool 60, reference plate 73, and dark box 65 that constitute the dental color measurement tool system of the present embodiment and the artificial tooth 50 to undergo color measurement will now be described in detail using FIGS. 1 to 5 and 11.

As shown in FIGS. 1 and 11, the artificial tooth 50 has a concave portion 50c that is formed inside the artificial tooth 50 and into which the above described abutment is inserted. The artificial tooth 50 includes an outer surface front portion (camera 2 side in a color measurement photographing state) 50a and an incisal portion 50b on a lower end side.

As shown in FIG. 1, the color measurement tool 60 has a tabular abutment plate 61, a pair of guide posts 63 and 64 that are vertically provided in the Y0 direction (vertical direction) on the underside of the abutment plate 61 in a condition in which the guide posts 63 and 64 are separated by a predetermined distance in the X0 direction (horizontal direction), and an abutment post 62 that is vertically provided in the Y0 direction on the underside of the abutment plate 61 between the guide posts 63 and 64.

A screw hole 61a for mounting the dark box 65 is provided in the abutment plate 61.

Convex portions 63a and 64a are provided at the distal end portion of the pair of guide posts 63 and 64, respectively. The convex portions 63a and 64a are engaging portions with respect to the contact cap 31 that is attached to the camera 2, and have a color measurement reference surface for positioning in the Y0 direction. In this connection, the guide posts 63 and 64 are secured to the abutment plate 61 with a screw, and it is possible to finely adjust the securing positions.

The abutment post 62 is provided with a contact surface 62a that serves as a color measurement reference surface for positioning in the optical axis direction and a pointed convex portion 62b as an artificial tooth mounting portion that is centered on the optical axis O in a color measurement photographing state. The contact surface 62a and the convex portion 62b are formed at a root portion (camera side). In this connection, the abutment post 62 is also secured with a screw to the abutment plate 61, and it is possible to finely adjust the securing position thereof.

As shown in FIG. 3, the end surfaces on the side opposite the camera of the convex portions 63a and 64a of the guide posts 63 and 64 are shaped to follow the arc of the radius R1 that is centered on the optical axis O. Further, the positions in the X0 direction of the convex portions 63a and 64a correspond to a space between the two columnar convex portions 31h of the contact cap 31.

The center of the pointed convex portion 62b of the abutment post 62 is positioned on the optical axis O of the arc of the radius R1 as described above.

The color measurement tool 60 is contacted against and mounted to the bite portion 31e of the contact cap 31 on the camera 2 side at the time of color measurement photographing. As shown in FIGS. 14 and 15, in that mounted state the convex portions 63a and 64a of the guide posts 63 and 64 are positioned so as to contact against the rear end surfaces (camera side) of the two columnar convex portions 31h of the contact cap 31. The radius R1 of the arc on which the convex portions 63a and 64a are disposed is smaller than the radius R0 of the cylindrical surface on which the wall portion 31j of the contact cap 31 is formed.

The reference plate 73 has a cuboid shape, and includes a color measurement reference surface 73a for positioning in the optical axis direction and a color measurement reference surface 73b for positioning in the Y0 direction.

As shown in FIG. 5, the dark box 65 includes a dark box main body 66 and a light-shielding frame 67. The dark box main body 66 is provided with an opening portion 66c into which the color measurement tool 60 is inserted, and a sponge frame 66a is adhered to the front face (camera side) thereof. A screw knob 68 for fixing the color measurement tool is provided on the upper surface of the dark box main body 66, and screw knobs 69 for fixing the light-shielding frame are provided on the side surfaces thereof.

The light-shielding frame 67 includes a frame body 67a that is made of sponge and has an opening portion 67b, and notch portions 67c and 67d. The notch portion 67c is provided so that the light-shielding frame 67 does not interfere with the color measurement tool fixing screw knob 68. The notch portions 67d are disposed on both sides of the light-shielding frame 67, respectively, to interfit with the screw knobs 69 for fixing the light-shielding frame. In this configuration, the light-shielding frame 67 is coupled to the dark box main body 66 side so as to cover the sponge frame 66a, and the dark box main body 66 is fixed by turning the screw knobs 69 for fixing the light-shielding frame that interfit with the notch portions 67d.

In the dental color measurement tool system having the aforementioned configuration, the artificial tooth 50 is inserted onto the convex portion 62b of the abutment post 62 of the color measurement tool 60 in a state in which wax 51 has been filled into the concave portion 50c thereof. Subsequently, the color measurement reference surface 73a of the reference plate 73 is butted against the contact surface 62a of the abutment post 62 of the color measurement tool 60, and the upper end in the longitudinal direction of the reference plate 73 is contacted against the abutment plate 61 (FIG. 11).

In this contacting state, the color measurement reference surface 73b is positioned on the same plane as the end surfaces of the convex portions 63a and 64a of the guide posts 63 and 64.

The photographer adjusts the relative position of the artificial tooth 50 with respect to the color measurement tool 60 while manually retaining the butting state of the reference plate 73 described above. More specifically, the photographer contacts the front face (camera side) 50a of the artificial tooth 50 against the color measurement reference surface 73a of the reference plate 73, and finely adjusts the vertical position and the position in the optical axis O direction of the artificial tooth 50 so that the incisal portion 50b of the artificial tooth 50 is aligned with the color measurement reference surface 73b of the reference plate 73 (FIG. 11).

The color measurement tool 60 in which positional adjustment of the artificial tooth 50 has been performed as described above is inserted inside the dark box main body 66 of the dark box 65 in the D0 direction (FIG. 1), and is secured therein by turning the screw knob 68. Further, the light-shielding frame 67 is mounted to the front (camera side) of the dark box main body 66, and the dark box main body 66 and the light-shielding frame 67 are unified by turning the screw knob 69.

The distal end portion of the camera 2 to which the contact cap 31 has been mounted is inserted from the light-shielding frame opening portion 67a into the dark box 65 that houses the color measurement tool 60. The insertion method is illustrated in FIGS. 12 and 13. First, the bite portion 31e at the distal end of the contact cap 31 is tilted slightly downward and inserted into the light-shielding frame opening portion 67a in the D21 direction (FIG. 12). At that time, the bite portion 31e is inserted so as to scoop up the artificial tooth 50. Thus, when the distal end portion of the camera 2 is rotated in the D22 direction (FIG. 13), as shown in FIGS. 14 and 15, a state is entered in which the convex portions 63a and 64a of the guide posts 63 and 64 of the color measurement tool 60 contact against the columnar convex portions 31h of the contact cap 31, and the distal end surfaces of the convex portions 63a and 64a and the incisal portion 50b of the artificial tooth 50 contact against the upper side portion 31f of the contact cap 31. This contacting state is one in which the color measurement tool 60 is in a set state for photographing with respect to the contact cap 31 and camera 2.

When the color measurement tool 60 is in the aforementioned set state for photographing, the position of the contact surface 62a of the abutment post 62 (in other words, the position of the reference plate color measurement reference surface 73a) corresponds with an optical-axis direction color measurement reference plane S0 that is the vicinity of the best focus position P0 in the optical axis O direction of the camera 2 in the set state for photographing. Further, the end surfaces of the convex portions 63a and 64a of the guide posts 63 and 64 (in other words, the position of the reference plate color measurement reference surface 73b) correspond with a Y0-direction (vertical direction) color measurement reference plane S1 as a range in which a favorable photographed image can be obtained of the photographing angle of view of the camera 2. In this connection, the aforementioned optical-axis direction color measurement reference plane S0 of the camera is a plane that is perpendicular to the optical axis O, and the Y0-direction (vertical direction) color measurement reference plane S1 is a plane that is parallel to the optical axis O.

The photographer retains the camera 2 in a relative set state for photographing between the color measurement tool 60 and the camera 2 and performs color measurement photographing. In the set state for photographing, the artificial tooth 50 is stably located at a suitable position for photographing with respect to the photographing window portion 12a of the camera 2 (opening portion 31a of the contact cap 31). More specifically, in the set state for photographing as described above, the front face (camera side) 50b of the artificial tooth 50 is positioned on the optical-axis direction color measurement reference plane S0 of the camera 2 on the optical axis O on the Y0 and X0 planes, and is at a position near the best focus position P0 of the camera 2. In other words, the front face (camera side) 50b of the artificial tooth 50 is within the depth-of-field range of the photographing optical system 18. At the same time, the incisal portion 50b of the artificial tooth 50 is positioned on the Y0-direction (vertical direction) color measurement reference plane SI of the camera 2, and the entire artificial tooth 50 is positioned within the opening portion 31a of the contact cap 31, in other words, within the photographing range inside the photographing window portion 12a of the camera top cover 12 (FIG. 14).

Further, in the aforementioned set state for photographing, a state is maintained in which extraneous light surrounding the artificial tooth 50 is blocked by the dark box 65.

Color measurement photographing is performed with the camera 2 in a state where the color measurement tool 60 and the camera 2 are in the set state described above. At the time of photographing, the photographer manually holds the camera 2, and after performing a desired photographic adjustment by rotating the focus ring 13 (FIG. 6) while observing the artificial tooth 50 that is the photographing subject on an LCD display portion (not shown), the photographer operates an operation switch button (not shown) to perform photographing. Photographed image data that is utilized for measuring the color of the artificial tooth 50 is obtained by this photographing.

In a case of applying the dental color measurement tool system of the present embodiment as described above, when positionally adjusting the artificial tooth 50 with respect to the color measurement tool 60 using the reference plate 73, by aligning the front face 50a and the incisal portion 50b of the artificial tooth 50 with the color measurement reference surfaces 73a and 73b of the reference plate 73 in a mounted state, it is possible to reliably position the front face 50a in the vicinity of the best focus position P0 of the camera 2 and reliably position the entire artificial tooth including the incisal portion 50b inside an angle of view with which a favorable photographed image can be obtained and perform color measurement photographing. By using the dark box 65 at the same time, extraneous light can be reliably blocked out so that favorable color measurement photograph data can be obtained.

Figure 16:
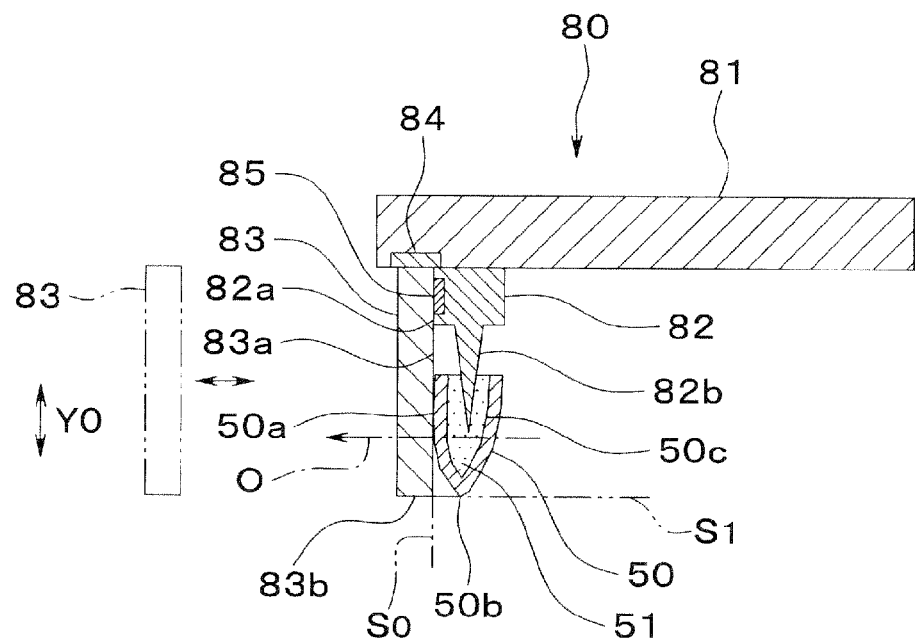
FIG. 16 is a sectional view along an optical axis that illustrates a state (artificial tooth positional adjustment state) in which a reference plate is brought in close contact with an abutment plate and an abutment post in a color measurement tool of a second embodiment.

Next, a color measurement tool included in a dental color measurement tool system that is the second embodiment of the present invention will be described using FIG. 16. FIG. 16 is a sectional view along the optical axis that illustrates a state (artificial tooth positional adjustment state) in which a reference plate is closely contacted against an abutment plate and an abutment post of a color measurement tool of the present embodiment.

A color measurement tool 80 of the present embodiment differs from the color measurement tool 60 of the first embodiment in that the color measurement tool 80 is configured so that the reference plate can be closely contacted against an abutment plate and an abutment post by magnetic force. The remaining configuration, that is, the abutment plate and the pair of guide posts and the like, is the same as that provided in the color measurement tool 60, and a dark box that is the same as the dark box 65 of the first embodiment is also applied. Hereunder, only the portions that are different from the first embodiment are described.

As shown in FIG. 16, the color measurement tool 80 has an abutment post 82 that is vertically provided in the Y0 direction of the abutment plate 81, and is provided with a reference plate 83 that can be closely contacted against the undersurface of an abutment plate 81 as an artificial tooth positional adjustment member and a contact surface 82a at the front on the camera side of the abutment post 82.

Similarly to the color measurement tool 60 of the first embodiment, the abutment post 82 of the color measurement tool 80 of the present embodiment is provided with a contact surface 82a that serves as a color measurement reference surface for positioning in the optical axis direction and a pointed convex portion 82b as an artificial tooth mounting portion that is centered on the optical axis O in a color measurement photographing state. The contact surface 82a and the convex portion 82b are formed at a root portion (camera side). A magnet 85 is embedded in the contact surface 82a. A magnet 84 is also embedded in the front side of the abutment post 82 at a position that is on the undersurface of the abutment plate 81.

The reference plate 83 is made with a magnetic material and has a color measurement reference surface 83a in the optical axis direction and a color measurement reference surface 83b in the Y0 direction. When the reference plate 83 is butted against the undersurface of the abutment plate 81 of the color measurement tool 80 and the contact surface 82a of the abutment post 82, the reference plate 83 is adhered thereto by the magnets 84 and 85 so that the color measurement reference surface 83a of the reference plate 83 adheres to the contact surface 82a and the color measurement reference surface 83b is aligned with the end surfaces of convex portions (not shown) of the guide posts. When the reference plate is in the adhered state, the color measurement reference surface 83a and the color measurement reference surface 83b are at positions that correspond to the optical-axis direction reference plane S0 and the Y0-direction (vertical direction) color measurement reference plane S1 on the camera side in the above described set state for photographing, respectively.

When mounting the artificial tooth 50 to the color measurement tool 80, the artificial tooth 50 is inserted onto the pointed convex portion 82b of the abutment post 82 in a state in which wax 51 has been filled in the concave portion 50c, similarly to the case of the color measurement tool 60. The reference plate 83 is then adhered by magnetic force to both the undersurface of the abutment plate 81 and the contact surface 82a of the abutment post 82. Accordingly, it is not necessary to manually hold the reference plate 83.

When the reference plate 83 is in the adhered state as described above, the photographer checks that the front face 50a of the artificial tooth 50 is contacting against the color measurement reference surface 83a of the reference plate 83. In this case, if the front face 50a is separate therefrom the photographer causes the front face 50a to contact against the color measurement reference surface 83a. The photographer also adjusts the position of the incisal portion 50b of the artificial tooth 50 so as to correspond with the color measurement reference surface 83b. After completing positional adjustment of the artificial tooth 50 as described above, the reference plate 83 is removed from the color measurement tool 80.

The color measurement tool 80 for which positional adjustment of the artificial tooth 50 has been performed is mounted in the dark box, and similarly to the first embodiment, the color measurement tool 80 is positioned and mounted at the bite portion 31e at the distal end of the contact cap 31 to place the color measurement tool 80 in the set state for photographing. More specifically, the color measurement tool 80 is placed in a set state in which the convex portions (not shown) of the guide posts are contacted against the columnar convex portions 31h of the contact cap 31 and the distal end surfaces of the convex portions are contacted against the upper side portions 31f of the contact cap 31. In this set state for photographing, the front face (camera side) 50b of the artificial tooth 50 is positioned on the optical-axis direction reference plane S0 of the camera 2 on the optical axis O on the Y0 and X0 planes, and is at a position near the best focus position P0 of the camera 2. In other words, the front face 50b of the artificial tooth 50 is within the depth-of-field range of the photographing optical system 18. At the same time, the incisal portion 50b of the artificial tooth 50 is positioned on the Y0-direction (vertical direction) color measurement reference plane S1 of the camera 2, and the entire artificial tooth 50 is positioned within the opening portion 31a of the contact cap 31. In other words, the incisal portion 50b is positioned within the photographing range inside the photographing window portion (opening portion) 12a of the camera top cover 12 and color measurement photographing of the artificial tooth 50 by the camera 2 is enabled.

The same advantages as in the first embodiment can be obtained by applying the color measurement tool 80 of the present embodiment as described above. In particular, in the case of the present embodiment, when adjusting the position of the artificial tooth 50, since the reference plate 83 is adhered to and retained at a specific position of the color measurement tool 80 by the magnetic force of magnets, it is not necessary to manually hold the reference plate 83 and thus the artificial tooth 50 can be adjusted with ease.

Figure 17:
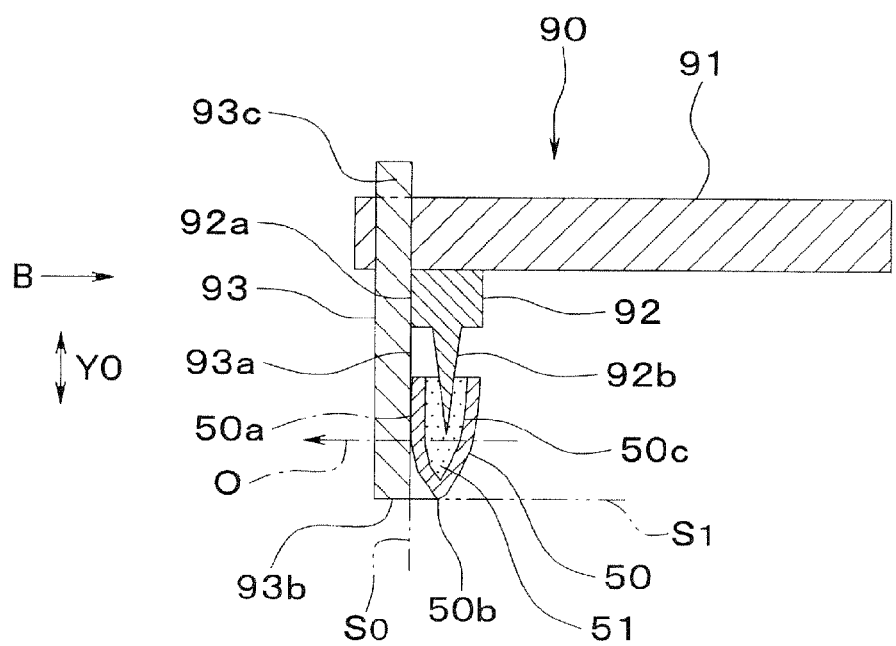
FIG. 17 is a sectional view along the optical axis that illustrates a state (artificial tooth positional adjustment state) in which a reference plate is butted against an abutment post of a color measurement tool according to a third embodiment.
Figure 18:
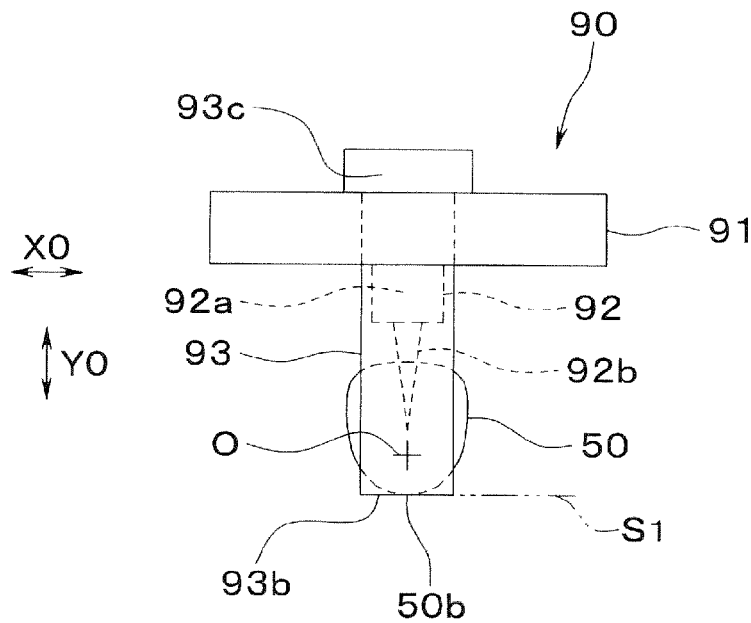
FIG. 18 is a view from the direction of arrow B in FIG. 17.
Figure 19:
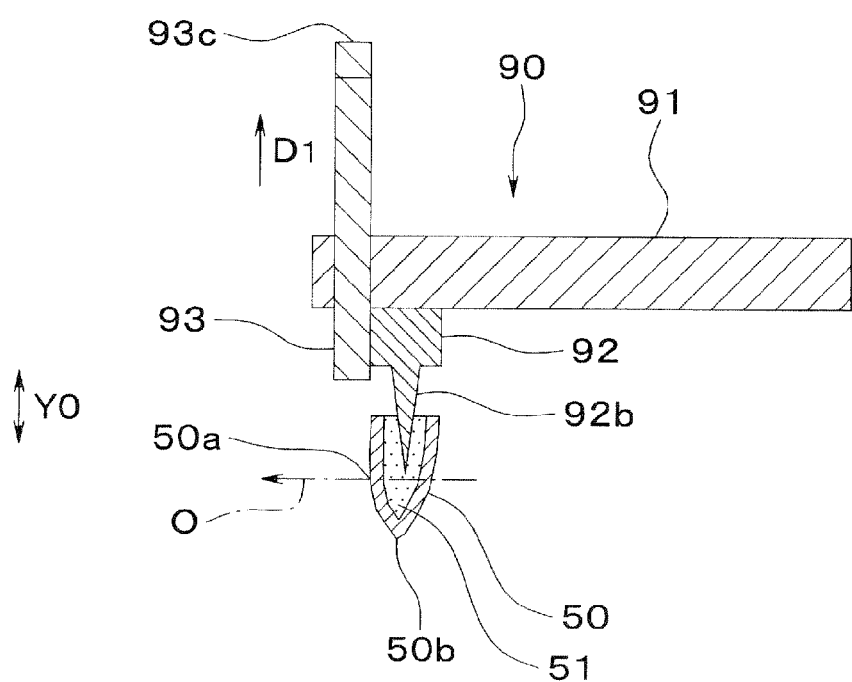
FIG. 19 is a sectional view along the optical axis that shows a state in which, in the color measurement tool shown in FIG. 17, the reference plate is withdrawn from the front face of the abutment post.

Next, a color measurement tool included in a dental color measurement tool system that is the third embodiment of the present invention will be described using FIGS. 17 to 19. FIG. 17 is a sectional view along an optical axis that illustrates a state (artificial tooth positional adjustment state) in which a reference plate is butted against an abutment post of the color measurement tool of the present embodiment. FIG. 18 is a view from the direction of arrow B in FIG. 17. FIG. 19 is a sectional view along the optical axis that shows a state in which, in the color measurement tool shown in FIG. 17, the reference plate has been withdrawn from the front face of the abutment post.

A color measurement tool 90 of the present embodiment differs from the color measurement tool 60 of the first embodiment in that the color measurement tool 90 includes a reference plate that is capable of a sliding movement in the Y0 direction (vertical direction) on the abutment plate. The remaining configuration, that is, the abutment plate, pair of guide posts, abutment post and the like, is the same as that provided in the color measurement tool 60, and a dark box that is the same as the dark box 65 of the first embodiment is also applied. Hereunder, only the portions that are different from the first embodiment are described.

The abutment post 92 of the color measurement tool 90 of the present embodiment is also provided with a contact surface 92a as a color measurement reference surface for positioning in the optical axis direction and a pointed convex portion 92b as an artificial tooth mounting portion that is centered on the optical axis O in a color measurement photographing state. The contact surface 92a and the convex portion 92b are formed at a root portion (camera side).

As shown in FIGS. 17 and 19, a reference plate 93 that is capable of a sliding movement in the Y0 direction on the front side (camera side) of the abutment post 92 is provided as an artificial tooth positional adjustment member on the abutment plate 91 of the color measurement tool 90.

The reference plate 93 has a color measurement reference surface 93a in the optical axis direction and a color measurement reference surface 93b in the Y0 direction (vertical direction), and is fitted in a guide hole of the abutment plate 91 in a state in which the reference plate 93 is slidable in the Y0 direction while contacting the contact surface 92a of the abutment post 92. In an adjustment position state in which the reference plate 93 has been moved downward in the Y0 direction and a stopper 93c contacted against the abutment plate 91, the color measurement reference surface 93b at the distal end thereof is on the same plane as the distal end surface of convex portions (not shown) of the guide posts, and as shown in FIGS. 17 and 18, is positioned on the color measurement reference plane S1 in the vertical direction of the camera 2 in the above described set state for photographing. The color measurement reference surface 93a abuts against the contact surface 92a of the abutment post 92, and is positioned on the color measurement reference plane S0 in the optical axis direction of the camera 2 in the aforementioned set state for photographing.

When mounting the artificial tooth 50 in the color measurement tool 90, the artificial tooth 50 is inserted onto the pointed convex portion 92b of the abutment post 92 in a state in which wax 51 has been filled in the concave portion 50c, similarly to the case of the color measurement tool 60. Subsequently, in a state in which the reference plate 93 butts against the contact surface 92a of the abutment post 92, the reference plate 93 is pushed downward until the stopper 93c contacts against the abutment plate 91 as described above.

The photographer confirms that the front face 50a of the artificial tooth 50 is contacting against the color measurement reference surface 93 a of the reference plate 93. If the front face 50a is separate therefrom, the photographer brings the front face 50a in contact with the color measurement reference surface 93a. The photographer also adjusts the position of the incisal portion 50b of the artificial tooth 50 so as to be aligned with the color measurement reference surface 93b. After completing the positional adjustment of the artificial tooth 50 as described above, the reference plate 93 is slid upward in the D1 direction to withdraw the reference plate 93 from the front (camera side) of the artificial tooth 50 (FIG. 19).

The color measurement tool 90 for which positional adjustment of the artificial tooth 50 has been performed is mounted in the dark box, and similarly to the first embodiment, the color measurement tool 90 is positioned and mounted at the bite portion 31e at the distal end of the contact cap 31 to place the color measurement tool 90 in the set state for photographing. Color measurement photographing of the artificial tooth 50 is performed with the camera 2 in this set state.

The same advantages as in the first embodiment can be obtained by applying the color measurement tool 90 of the present embodiment as described above. In particular, in the case of the present embodiment, since the reference plate 93 is mounted in a slidable state on the abutment plate 91, the reference plate 93 has excellent handling properties and the reference plate 93 can be slidingly moved to the front of the abutment post 92 to adjust the position of the artificial tooth 50. There is thus the advantage that an operation to adjust the artificial tooth 50 can be carried out with ease.

Figure 20:
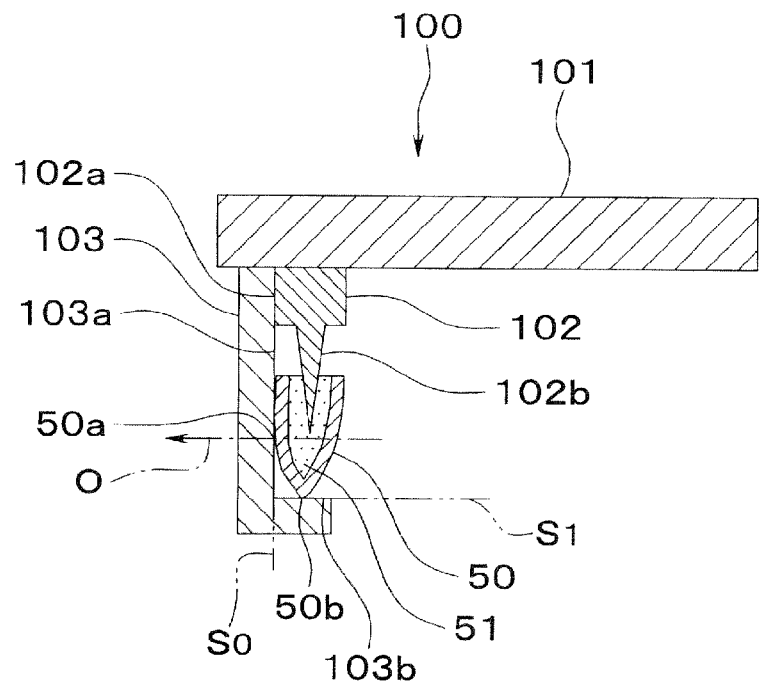
FIG. 20 is a sectional view along an optical axis that illustrates a state (artificial tooth positional adjustment state) in which a reference plate is butted against an abutment post of a color measurement tool according to a fourth embodiment.
Figure 21:
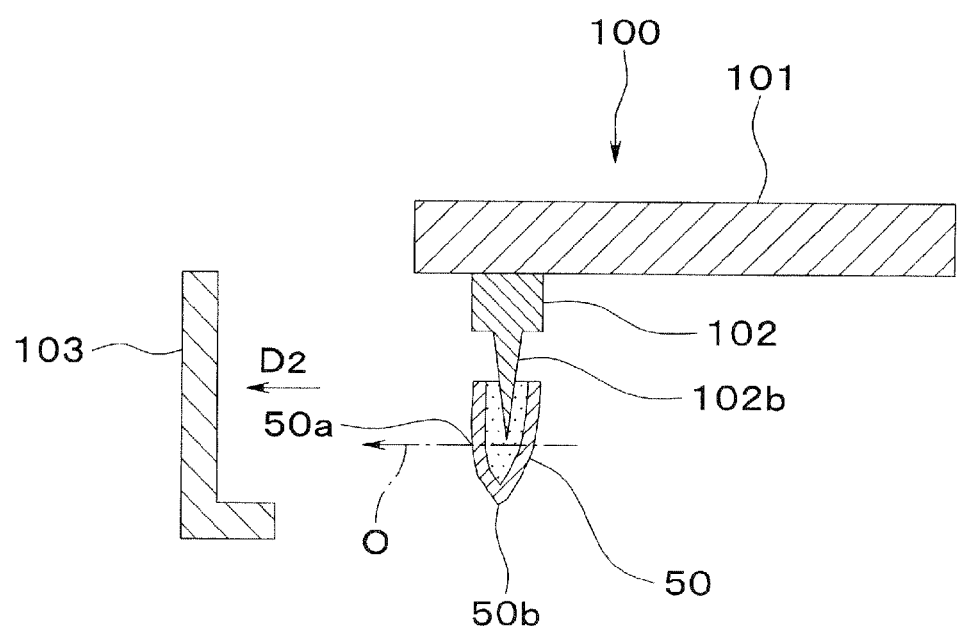
FIG. 21 is a sectional view along the optical axis that shows a state in which, in the color measurement tool shown in FIG. 20, the reference plate is removed from the front face of the abutment post.

Next, a color measurement tool included in a dental color measurement tool system that is the fourth embodiment of the present invention will be described using FIGS. 20 and 21. FIG. 20 is a sectional view along an optical axis that illustrates a state (artificial tooth positional adjustment state) in which a reference plate is butted against an abutment post of a color measurement tool according to the present embodiment. FIG. 21 is a sectional view along the optical axis that shows a state in which, in the color measurement tool shown in FIG. 20, the reference plate is removed from the front face of the abutment post.

A color measurement tool 100 of the present embodiment differs from the color measurement tool 60 of the first embodiment in that the color measurement tool 100 includes an L-shaped reference plate that can be detachably mounted to the abutment post. The remaining configuration, that is, the abutment plate, pair of guide posts, abutment post and the like, is the same as that provided in the color measurement tool 60, and a dark box that is the same as the dark box 65 of the first embodiment is also applied. Hereunder, only the portions that are different from the first embodiment are described.

Similarly to the first embodiment, an abutment post 102 of the color measurement tool 100 of the present embodiment is provided with a contact surface 102a as a color measurement reference surface for positioning in the optical axis direction and a pointed convex portion 102b as an artificial tooth mounting portion that is centered on the optical axis O in a color measurement photographing state. The contact surface 102a and the convex portion 102b are formed at a root portion (camera side).

As shown in FIGS. 20 and 21, a reference plate 103 that can be detachably mounted to the front side (camera side) of the abutment post 102 on the abutment plate 101 is provided as an artificial tooth positional adjustment member for the color measurement tool 100.

The reference plate 103 is formed in an L shape. In this case, the inner face of the upright portion in the Y0 direction serves as a color measurement reference surface 103a in the optical axis direction, and the inside of the L-shaped distal end portion serves as a color measurement reference surface 103b in the Y0 direction. One end face of the reference plate 103 is butted against the undersurface of the abutment plate 101, and the color measurement reference surface 103a is brought in close contact with the contact surface 102a of the abutment post 102 to thereby mount the reference plate 103 to the color measurement tool 100. As shown in FIG. 20, in this mounting state, the color measurement reference surface 103a abuts against the contact surface 102a of the abutment post 102 and is positioned on the color measurement reference plane S0 in the optical axis direction of the camera 2 in the above described set state for photographing. The color measurement reference surface 103b of the L-shaped distal end portion corresponds to the distal end surface of the convex portions (not shown) of the guide posts, and is positioned on the color measurement reference plane S1 in the vertical direction of the camera 2 in the above described set state for photographing.

When mounting the artificial tooth 50 in the color measurement tool 100, the artificial tooth 50 is inserted onto the pointed convex portion 102b of the abutment post 102 in a state in which wax 51 has been filled in the concave portion 50c, similarly to the case of the color measurement tool 60, in a state in which the reference plate 103 is separated from the color measurement tool 100. The reference plate 103 is then contacted against the undersurface of the abutment plate 101 of the color measurement tool 100 and also butted against the contact surface 102a of the abutment post 102, to thus enter a mounted state.

While manually retaining the butting state of the reference plate 103 as described above, the photographer confirms that the front face 50a of the artificial tooth 50 abuts against the color measurement reference surface 103a of the reference plate 103. If the front face 50a is separate therefrom, the photographer contacts the front face 50a against the color measurement reference surface 103a. The photographer also adjusts the position of the incisal portion 50b of the artificial tooth 50 so as to abut against the color measurement reference surface 103b. After completing the positional adjustment of the artificial tooth 50 as described above, the reference plate 103 is moved to the D2 side to remove the reference plate 103 from the color measurement tool 100 (FIG. 21).

The color measurement tool 100 for which positional adjustment of the artificial tooth 50 has been performed is mounted in the dark box, and similarly to the first embodiment, the color measurement tool 100 is positioned and mounted at the bite portion 31e at the distal end of the contact cap 31 to place the color measurement tool 100 in the set state for photographing. In this set state, color measurement photographing of the artificial tooth 50 is performed with the camera 2.

According to the color measurement tool 100 of the present embodiment as described above, the same advantages as those of the first embodiment can be obtained. In particular, in the case of the present embodiment, since the reference plate 103 is provided with color measurement reference surfaces in both the optical axis direction and the vertical direction against which it is possible to butt the artificial tooth 50, work to positionally adjust the artificial tooth 50 is facilitated and an exact positional adjustment is enabled.

Figure 22:
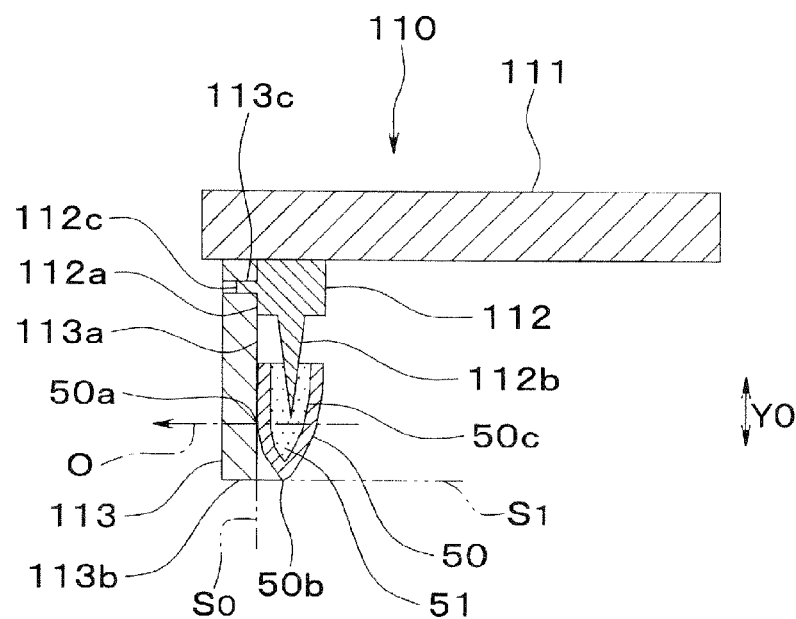
FIG. 22 is a sectional view along an optical axis that illustrates a state (artificial tooth positional adjustment state) in which a reference plate is mounted to an abutment post of a color measurement tool according to a fifth embodiment.
Figure 23:
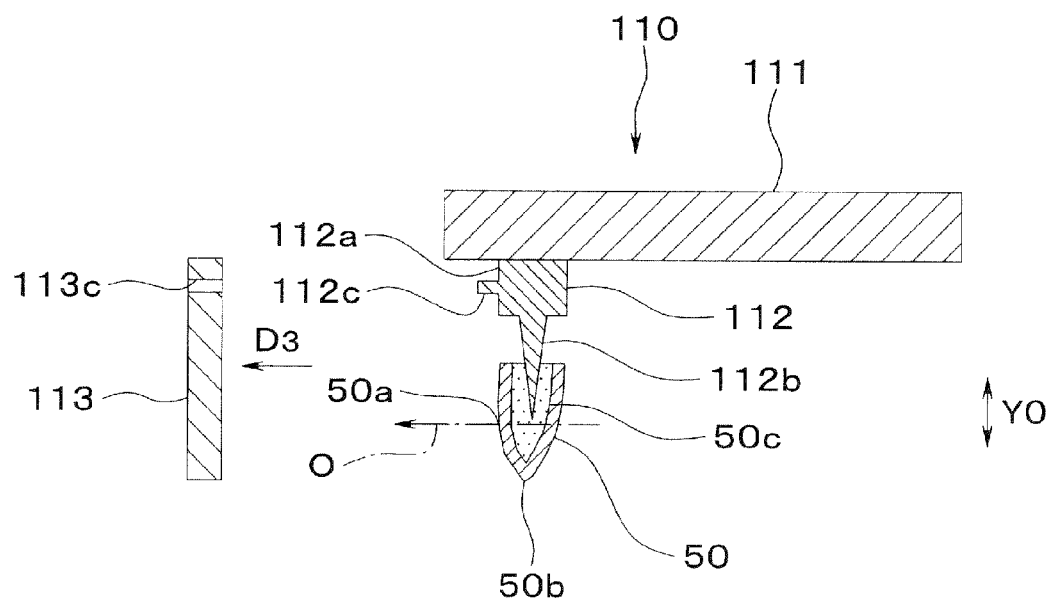
FIG. 23 is a sectional view along the optical axis that shows a state in which, in the color measurement tool shown in FIG. 22, the reference plate is removed from the front face of the abutment post.

Next, a color measurement tool included in a dental color measurement tool system that is the fifth embodiment of the present invention will be described using FIGS. 22 and 23. FIG. 22 is a sectional view along an optical axis that illustrates a state (artificial tooth positional adjustment state) in which a reference plate is mounted to an abutment post of a color measurement tool according to the present embodiment. FIG. 23 is a sectional view along the optical axis that shows a state in which, in the color measurement tool shown in FIG. 22, the reference plate is removed from the front of the abutment post.

A color measurement tool 110 of the present embodiment differs from the color measurement tool 60 of the first embodiment in that the color measurement tool 110 includes a reference plate mounted by fitting a pin into the reference plate. The remaining configuration, that is, the abutment plate, pair of guide posts, abutment post, and the like is the same as that provided in the color measurement tool 60, and a dark box that is the same as the dark box 65 of the first embodiment is also applied. Hereunder, only the portions that are different from the first embodiment are described.

An abutment post 112 of the color measurement tool 110 of the present embodiment is provided with a contact surface 112a as a color measurement reference surface for positioning in the optical axis direction and a pointed convex portion 112b as an artificial tooth mounting portion that is centered on the optical axis O in a color measurement photographing state. The contact surface 112a and the convex portion 112b are formed at a root portion (camera side). A positioning pin (fitting portion) 112c is provided in the contact surface 112a.

Further, as shown in FIGS. 22 and 23, a reference plate 113 that can be mounted to the front side (camera side) of the abutment post 112 of the abutment plate 111 by fitting to a pin is provided as an artificial tooth positional adjustment member in the color measurement tool 110.

The reference plate 113 has a color measurement reference surface 113a in the optical axis direction, a color measurement reference surface 113b in the Y0 direction, and a pin hole 113 (fitting portion) c that interfits with a positioning pin 112c of the abutment post 112. The reference plate 113 is mounted in a positioned state with respect to the contact surface 112a of the abutment post 112 by fitting the positioning pin 112c into the pin hole 113c. In the above described positioned state, the color measurement reference surface 113b at the distal end of the reference plate 113 is on the same plane as the distal end surface of convex portions (not shown) of the guide posts, and as shown in FIG. 22, is positioned on the color measurement reference plane S1 in the vertical direction of the camera 2 in the set state for photographing. Further, since the color measurement reference surface 113a abuts against the contact surface 112a of the abutment post 112, the color measurement reference surface 113a is positioned on the color measurement reference plane S0 in the optical axis direction of the camera 2 in the set state for photographing.

When mounting the artificial tooth 50 in the color measurement tool 110, the artificial tooth 50 is inserted onto the pointed convex portion 112b of the abutment post 112 in a state in which wax 51 has been filled in the concave portion 50c, similarly to the case of the color measurement tool 60. The front face 50a of the artificial tooth 50 is caused to contact against the color measurement reference surface 113a of the reference plate 113 that is mounted and retained by engagement of the pin at the contact surface 112a of the abutment post 112. Further, the photographer aligns the incisal portion 50b of the artificial tooth 50 with the color measurement reference surface 113b. After completing positional adjustment of the artificial tooth 50 as described above, the photographer moves the reference plate 113 in the D3 direction to remove the reference plate 113 from the color measurement tool 110 (FIG. 23).

The color measurement tool 110 for which positional adjustment of the artificial tooth 50 has been performed is mounted in the dark box and, similarly to the first embodiment, the color measurement tool 110 is positioned at the bite portion 31e at the distal end of the contact cap 31 to place the color measurement tool 110 in the set state for photographing. In this set state, color measurement photographing of the artificial tooth 50 is performed with the camera 2.

The same advantages as those of the first embodiment can be obtained by applying the color measurement tool 110 of the present embodiment as described above. In particular, in the case of the present embodiment, when adjusting the position of the artificial tooth 50, since the reference plate 113 can be retained in place at the abutment post 112 without manually pressing the reference plate 113, an operation to adjust the artificial tooth 50 is performed with ease.

Figure 24:
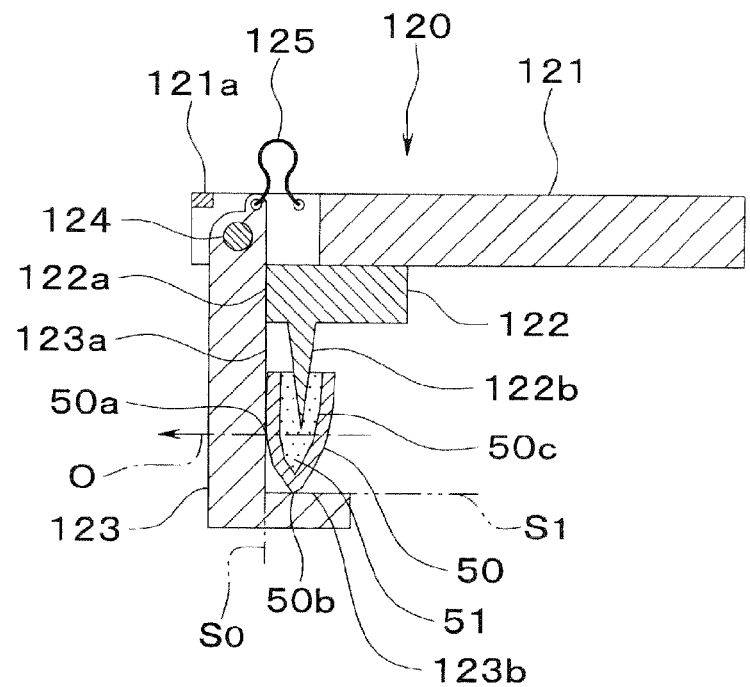
FIG. 24 is a sectional view along an optical axis that illustrates a state (artificial tooth positional adjustment state) in which a reference plate is butted against an abutment post of a color measurement tool according to a sixth embodiment.
Figure 25:
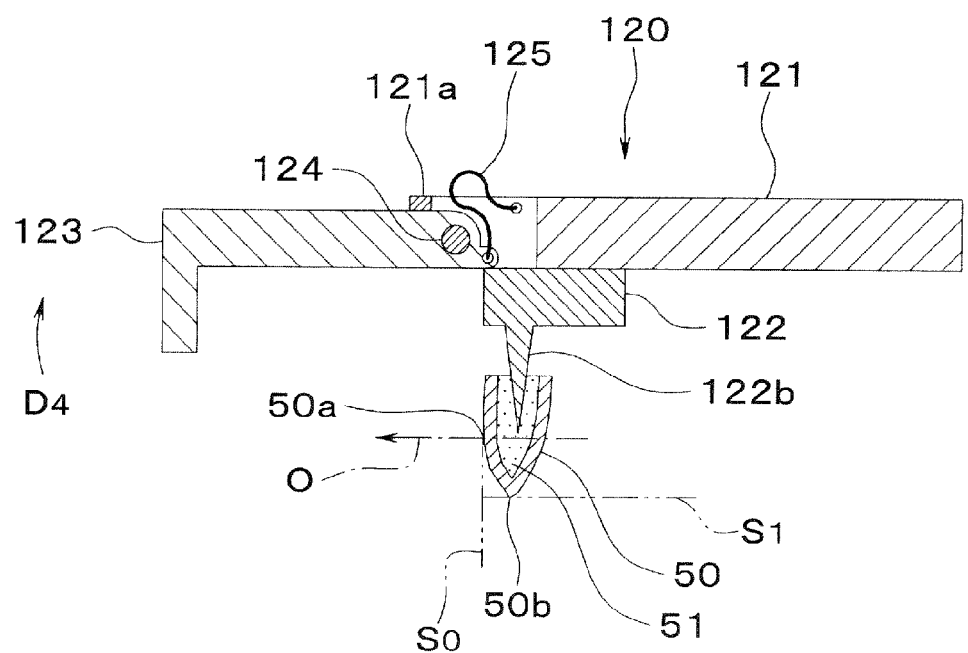
FIG. 25 is a sectional view along the optical axis that shows a state in which, in the color measurement tool shown in FIG. 24, the reference plate has been withdrawn.

Next, a color measurement tool included in a dental color measurement tool system that is the sixth embodiment of the present invention will be described using FIGS. 24 and 25. FIG. 24 is a sectional view along an optical axis that illustrates a state (artificial tooth positional adjustment state) in which a reference plate is butted against an abutment post of a color measurement tool of the present embodiment. FIG. 25 is a sectional view along the optical axis that shows a state in which, with respect to the color measurement tool shown in FIG. 24, the reference plate has been withdrawn.

A color measurement tool 120 of the present embodiment differs from the color measurement tool 60 of the first embodiment in the that the color measurement tool 120 includes a reference plate that is rotatable with respect to the abutment post of the color measurement tool. The remaining configuration, that is, the abutment plate, pair of guide posts, abutment post, and the like is the same as that provided in the color measurement tool 60, and a dark box that is the same as the dark box 65 of the first embodiment is also applied. Hereunder, only the portions that are different from the first embodiment are described.

Similarly to the first embodiment, an abutment post 122 of the color measurement tool 120 of the present embodiment is provided with a contact surface 122a as a color measurement reference surface for positioning in the optical axis direction and a pointed convex portion 122b as an artificial tooth mounting portion that is centered on the optical axis O in a color measurement photographing state. The contact surface 122a and the convex portion 122b are formed at a root portion (camera side).

As shown in FIGS. 24 and 25, a reference plate 123 that can be rotated from an adjustment position at the front (camera side) of the abutment post to a withdrawn position at which the reference plate 123 is withdrawn from the front of the abutment post is provided as an artificial tooth positional adjustment member on an abutment plate 121 of the color measurement tool 120. The reference plate 123 is supported by a support shaft 124.

The reference plate 123 is formed in an L shape. In this case, the inner surface of an upright arm portion serves as a color measurement reference surface 123a in the optical axis direction, and the inner surface of the L-shaped distal end portion serves as a color measurement reference surface 123b in the Y0 direction. The reference plate 123 is switchingly urged in two directions by a U-shaped urging spring 125. When an operation is performed to rotate the reference plate 123 as far as a predetermined position in the counterclockwise direction, the reference plate 123 is urged in the same direction and enters a state in which it is in an upright position (artificial tooth positional adjustment state) as shown in FIG. 24. When an operation is performed to rotate the reference plate 123 as far as a predetermined position in the clockwise direction (D4 direction) from the adjustment position state shown in FIG. 24, the reference plate 123 is urged in the same direction to abut against a stopper 121a on the abutment plate side and enter a withdrawn position state as shown in FIG. 25.

In the state shown in FIG. 24, the color measurement reference surface 123a of the reference plate 123 abuts against the contact surface 122a of the abutment post 122, and the color measurement reference surface 123a is positioned on the color measurement reference plane S0 in the optical axis direction of the camera 2 in the set state for photographing. The color measurement reference surface 123b of the L-shaped distal end portion is on the same plane as the distal end surface of the convex portions (not shown) of the guide posts, and is positioned on the color measurement reference plane S1 in the vertical direction of the camera 2.

When mounting the artificial tooth 50 in the color measurement tool 120, the reference plate 123 is rotated clockwise to withdraw the reference plate 123 to the position shown in FIG. 25, and the artificial tooth 50 is inserted onto the pointed convex portion 122b of the abutment post 122 in a state in which wax 51 has been filled in the concave portion 50c. The reference plate 123 is then rotated counterclockwise to place the reference plate 123 in the artificial tooth positional adjustment state shown in FIG. 24.

The photographer confirms that the front face 50a of the artificial tooth 50 abuts against the color measurement reference surface 123a of the reference plate 123 in the state shown in FIG. 24. If the front face 50a is separate therefrom, the photographer contacts the front face 50a against the color measurement reference surface 123a. The photographer also adjusts the position of the incisal portion 50b of the artificial tooth 50 so that the incisal portion 50b abuts against the color measurement reference surface 123b. After completing the positional adjustment of the artificial tooth 50 as described above, the reference plate 123 is rotated clockwise so as to withdraw the reference plate 123 from the front of the artificial tooth 50 as shown in FIG. 25.

The color measurement tool 120 for which positional adjustment of the artificial tooth 50 has been performed is mounted in the dark box, and similarly to the first embodiment, the color measurement tool 120 is positioned and mounted at the bite portion 31e at the distal end of the contact cap 31 to place the color measurement tool 120 in the set state for photographing. In this set state, color measurement photographing of the artificial tooth 50 is performed with the camera 2.

According to the color measurement tool 120 of the present embodiment described above it is possible to obtain the same advantages as those of the first embodiment. In particular, in the case of the present embodiment, with the reference plate 123 it is possible to perform exact positional adjustment of an artificial tooth by means of color measurement reference surfaces in both the optical axis direction and the vertical direction. Further, since the reference plate 123 is rotatingly urged between both an upright position (artificial tooth positional adjustment position) and a withdrawn position, operation of the reference plate 123 is simple. Furthermore, since positional adjustment of the artificial tooth 50 can be performed even in a state when the photographer's hands are away from the reference plate 123, the adjustment work can be performed with ease.

Figure 26:
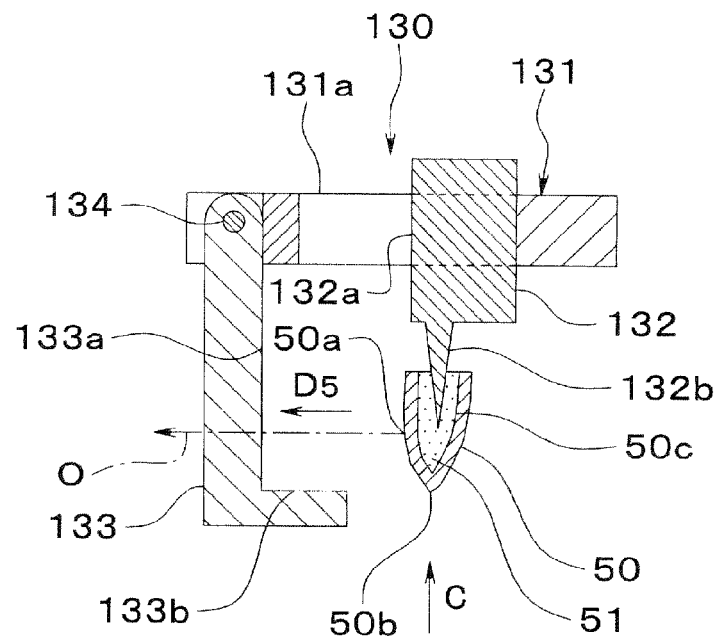
FIG. 26 is a sectional view along the optical axis in an artificial tooth mounting state (state in which reference plate is upright and abutment post is retracted) of a color measurement tool according to a seventh embodiment.
Figure 27:
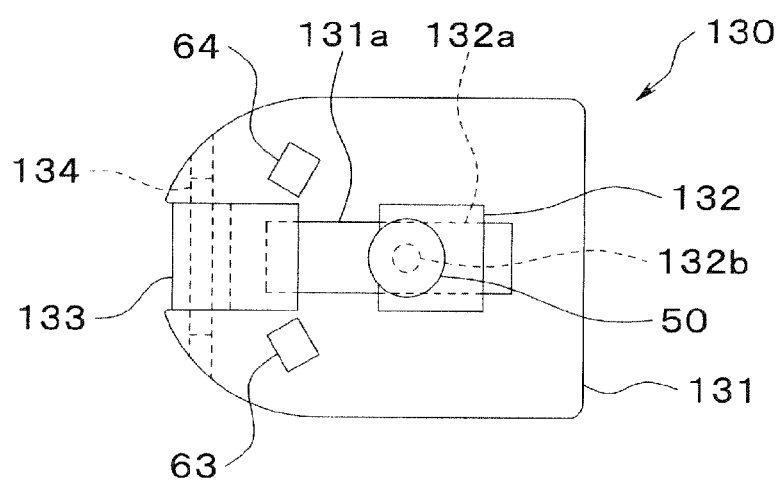
FIG. 27 is a view from the direction of arrow C in FIG. 26.
Figure 28:
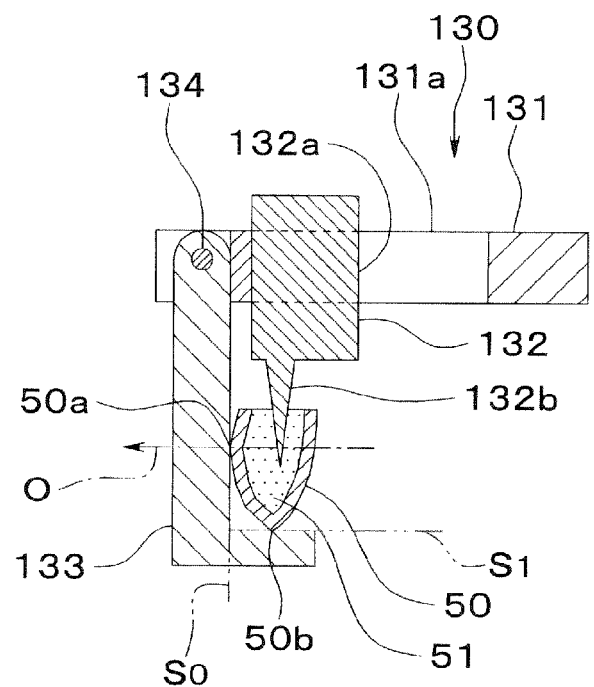
FIG. 28 is a sectional view along the optical axis in an artificial tooth positional adjustment state of the color measurement tool shown in FIG. 26.
Figure 29:
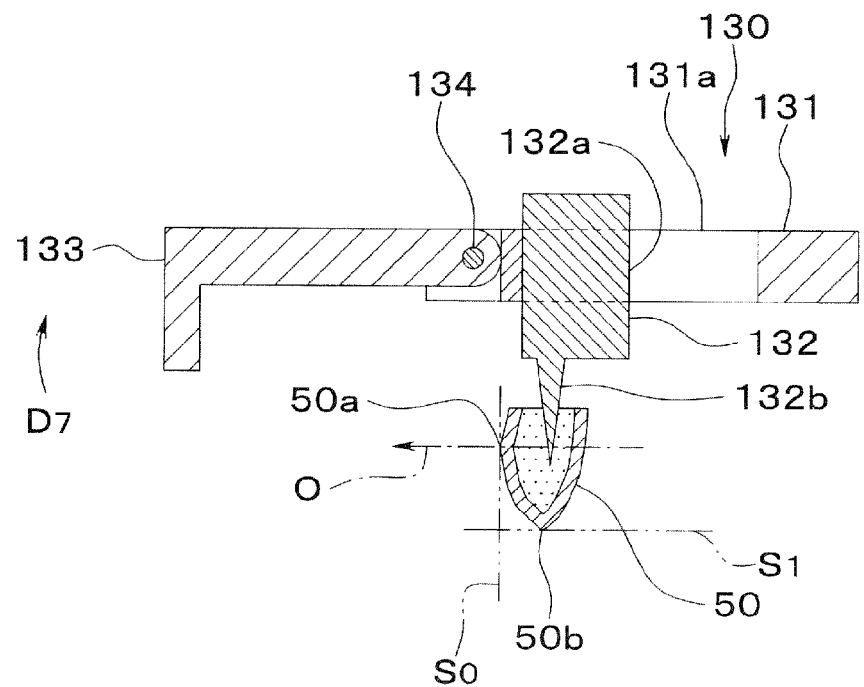
FIG. 29 is a sectional view along the optical axis in a state in which the reference plate of the above described color measurement tool has been withdrawn.

Next, a color measurement tool included in a dental color measurement tool system that is the seventh embodiment of the present invention will be described using FIGS. 26 to 29. FIG. 26 is a sectional view along the optical axis in an artificial tooth mounting state (state in which reference plate is upright and abutment post is retracted) of a color measurement tool according to the present embodiment. FIG. 27 is a view from the direction of arrow C in FIG. 26. FIG. 28 is a sectional view along the optical axis in an artificial tooth positional adjustment state of the color measurement tool shown in FIG. 26. FIG. 29 is a sectional view along the optical axis in a state in which the reference plate of the above described color measurement tool is withdrawn.

A color measurement tool 130 of the present embodiment differs from the color measurement tool 60 of the first embodiment in that the color measurement tool 130 includes a slidable abutment post and a rotatable reference plate. The remaining configuration, that is, the abutment plate and the pair of guide posts, is the same as that provided in the color measurement tool 60, and a dark box that is the same as the dark box 65 of the first embodiment is also applied. Hereunder, only the portions that are different from the first embodiment are described.

A post base portion 132a of an abutment post 132 of the color measurement tool 130 of the present embodiment is guided by a guide groove 131a of an abutment plate 131, and is supported so as to be capable of a sliding movement along the optical axis O direction. As a result, the abutment post 132 is arranged so as to be movable between a rearward position (FIG. 26) on a side opposite the camera as an artificial tooth mounting position and a front position (FIG. 28) on the camera side as an adjustment position. In this connection, the abutment post 132 is also provided with a pointed convex portion 132b as an artificial tooth mounting portion that is centered on the optical axis O in a color measurement photographing state.

Further, the abutment plate 131 of the color measurement tool 130 is also provided with a reference plate 133 as an artificial tooth positional adjustment member. The reference plate 133 is supported by a support shaft 134 so as to be rotatable from an upright position (adjustment position) at the front (camera side) of the abutment post, as shown in FIG. 26, to a withdrawn position.

The reference plate 133 is formed in an L shape, and has an optical-axis direction color measurement reference surface 133a at the inner surface of an arm portion and a Y0-direction color measurement reference surface 133b at the inner surface of an L-shaped distal end portion. When the reference plate 133 is in an upright position (FIGS. 26 and 28), the lower part of the color measurement reference surface 133a abuts against a groove surface of the abutment plate 131 to position the color measurement reference surface 133a on the color measurement reference plane S0 in the optical axis direction on the camera side in a color measurement photographing state. Further, the color measurement reference surface 133b of the L-shaped distal end portion is positioned on the same plane as the distal end surface of the convex portions (not shown) of the guide posts 63 and 64, and is located on the color measurement reference plane S1 in the vertical direction on the camera side.

When mounting the artificial tooth 50 in the color measurement tool 130, as shown in FIG. 26, the reference plate 133 is placed in an upright state and the abutment post 132 is retracted in the optical axis O direction. Then, similarly to the case of the color measurement tool 60, the artificial tooth 50 is inserted onto the pointed convex portion 132b of the abutment post 132 in a state in which wax 51 has been filled in the concave portion 50c.

The abutment post 132 is moved forward in the D5 direction (camera side) so as to cause the front face 50a of the artificial tooth 50 to abut against the color measurement reference surface 133a of the reference plate 133 as shown in FIG. 28. The photographer then performs positional adjustment so that the incisal portion 50b of the artificial tooth 50 abuts against the color measurement reference surface 133b. After completing the positional adjustment of the artificial tooth 50 as described above, the reference plate 133 is rotated clockwise so as to withdraw the reference plate 133 away from the front of the artificial tooth 50 as shown in FIG. 29.

The color measurement tool 130 for which positional adjustment of the artificial tooth 50 has been performed is mounted in the dark box, and similarly to the first embodiment, the color measurement tool 130 is positioned and mounted at the bite portion 31e at the distal end of the contact cap 31 to place the color measurement tool 130 in the set state for photographing. In this set state, color measurement photographing of the artificial tooth 50 is performed with the camera 2.

According to the color measurement tool 130 of the present embodiment described above it is possible to obtain the same advantages as those of the first embodiment. In particular, in the case of the present embodiment, after retracting the abutment post 132 to the artificial tooth mounting position in the optical axis O direction and mounting the artificial tooth 50, since it is possible to slidingly move the abutment post 132 to the adjustment position and cause the artificial tooth to butt against the reference plate 133 that is in an upright position to perform positional adjustment, work to positionally adjust the artificial tooth with respect to the color measurement reference planes S0 and S1 on the camera side can be performed with ease.

In this connection, a configuration may also be adopted in which the U-shaped urging spring 125 of the sixth embodiment is mounted to the reference plate 133 so that the reference plate 133 is switchingly urged in two directions.

Figure 30:
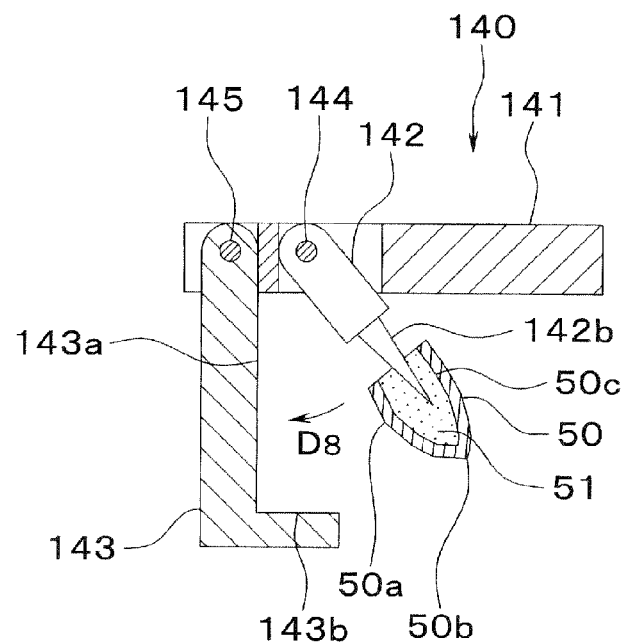
FIG. 30 is a sectional view along the optical axis in an artificial tooth mounting state (state in which reference plate is upright and abutment post is retracted) of a color measurement tool according to an eighth embodiment.
Figure 31:
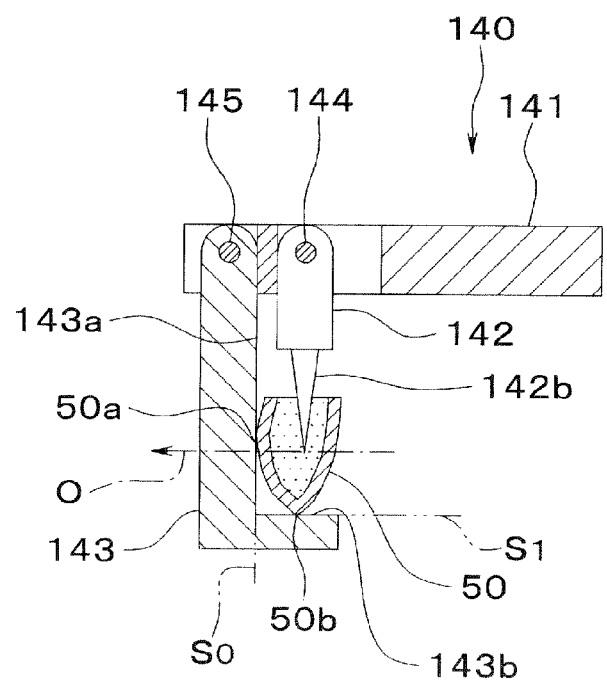
FIG. 31 is a sectional view along the optical axis in an artificial tooth positional adjustment state of the color measurement tool shown in FIG. 30.
Figure 32:
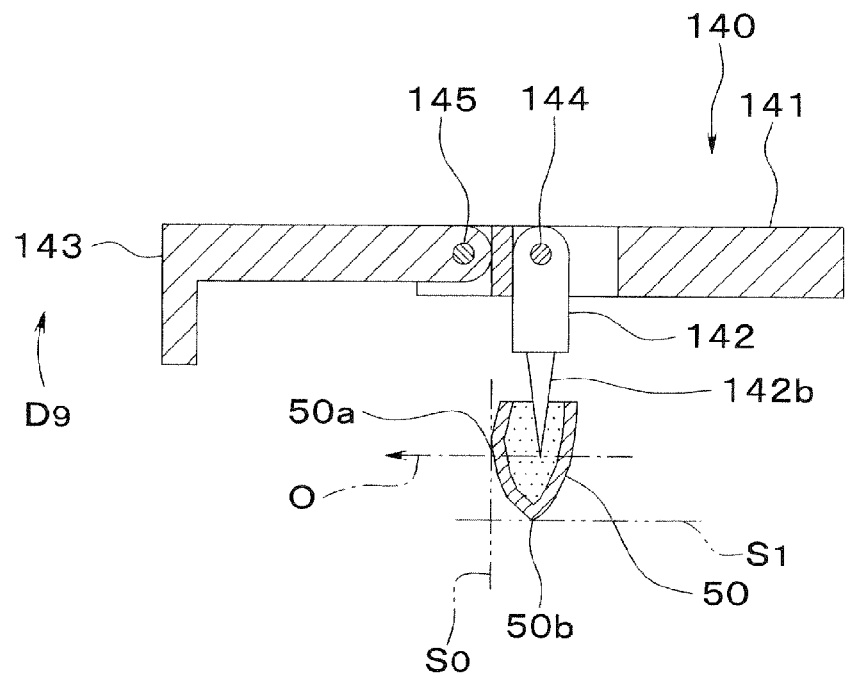
FIG. 32 is a sectional view along the optical axis in a state in which the reference plate of the color measurement tool shown in FIG. 30 has been withdrawn.

Next, a color measurement tool included in a dental color measurement tool system that is the eighth embodiment of the present invention will be described using FIGS. 30 to 32. FIG. 30 is a sectional view along the optical axis in an artificial tooth mounting state (state in which reference plate is upright and abutment post is retracted) of the color measurement tool according to the present embodiment. FIG. 31 is a sectional view along the optical axis in an artificial tooth positional adjustment state of the color measurement tool shown in FIG. 30. FIG. 32 is a sectional view along the optical axis in a state in which the reference plate of the color measurement tool shown in FIG. 30 is withdrawn.

A color measurement tool 140 of the present embodiment differs from the color measurement tool 60 of the first embodiment in that the color measurement tool 140 includes an abutment post and a reference plate that are respectively rotatable with respect to the abutment plate. The remaining configuration, that is, the abutment plate and the pair of guide posts, is the same as that provided in the color measurement tool 60, and a dark box that is the same as the dark box 65 of the first embodiment is also applied. Hereunder, only the portions that are different from the first embodiment are described.

An abutment post 142 of the color measurement tool 140 of the present embodiment is supported in an abutment plate 141 by a support shaft 144, and is arranged to be rotatable between a rearward position (FIG. 30) on a side opposite the camera as an artificial tooth mounting position and a frontward position (FIG. 31) on the camera side as an adjustment position. Further, the abutment post 142 has a pointed convex portion 142b as an artificial tooth mounting portion that is centered on the optical axis O in a color measurement photographing state.

A reference plate 143 as an artificial tooth positional adjustment member is supported by a support shaft 145 on the abutment plate 141 of the color measurement tool 140. More specifically, as shown in FIGS. 31 and 32, the reference plate 143 is supported in a condition in which the reference plate 143 can rotate to a withdrawn position from an upright position that is an adjustment position at the front of the abutment post 142.

The reference plate 143 is formed in an L shape, and has an optical-axis direction color measurement reference surface 143a at the inner surface of an arm portion and a Y0-direction color measurement reference surface 143b at the inner surface of an L-shaped distal end portion. When the reference plate 143 is at an upright position (FIGS. 30 and 31), the lower part of the color measurement reference surface 143a abuts against a groove surface of the abutment plate 141 to position the color measurement reference surface 143a on the color measurement reference plane S0 in the optical axis direction on the camera side in a color measurement photographing state. Further, the color measurement reference surface 143b of the L-shaped distal end portion is on the same plane as the distal end surface of the convex portions (not shown) of the guide posts, and is positioned on the color measurement reference plane S1 in the vertical direction on the camera side.

When mounting the artificial tooth 50 in the color measurement tool 140, as shown in FIG. 30, the reference plate 143 is placed upright and the abutment post 142 is tilted to a rearward position. In that state, similarly to the case of the color measurement tool 60, the artificial tooth 50 is inserted onto the pointed convex portion 142b of the abutment post 142 in a state in which wax 51 has been filled in the concave portion 50c.

The abutment post 142 is then rotated in the D8 direction to assume an upright state (FIG. 31) and cause the front face 50a of the artificial tooth 50 to abut against the color measurement reference surface 143a of the reference plate 143. The photographer then performs positional adjustment so that the incisal portion 50b of the artificial tooth 50 abuts against the color measurement reference surface 143b. After completing the positional adjustment of the artificial tooth 50 as described above, the reference plate 143 is rotated clockwise in the D9 direction so as to withdraw the reference plate 143 away from the front of the artificial tooth 50 as shown in FIG. 32.

The color measurement tool 140 for which positional adjustment of the artificial tooth 50 has been performed is mounted in the dark box, and similarly to the first embodiment, the color measurement tool 140 is positioned and mounted at the bite portion 31e at the distal end of the contact cap 31 to place the color measurement tool 140 in the set state for photographing. In this set state, color measurement photographing of the artificial tooth 50 is performed with the camera 2.

The same advantages as those of the first embodiment can be obtained according to the color measurement tool 140 of the present embodiment as described above. In particular, in the case of the present embodiment, positional adjustment of the artificial tooth can be performed with respect to the color measurement reference planes S0 and S1 on the camera side by rotating the abutment post 142 to a withdrawn position, mounting the artificial tooth 50, and then causing the artificial tooth 50 to abut against the reference plate 143 that is in an upright position. Thus, an operation to mount and adjust the artificial tooth can be performed with ease.

In this connection, a configuration may also be adopted in which the U-shaped urging spring 125 of the sixth embodiment is mounted to the reference plate 143 so that the reference plate 143 is switchingly urged in two directions.

Figure 33:
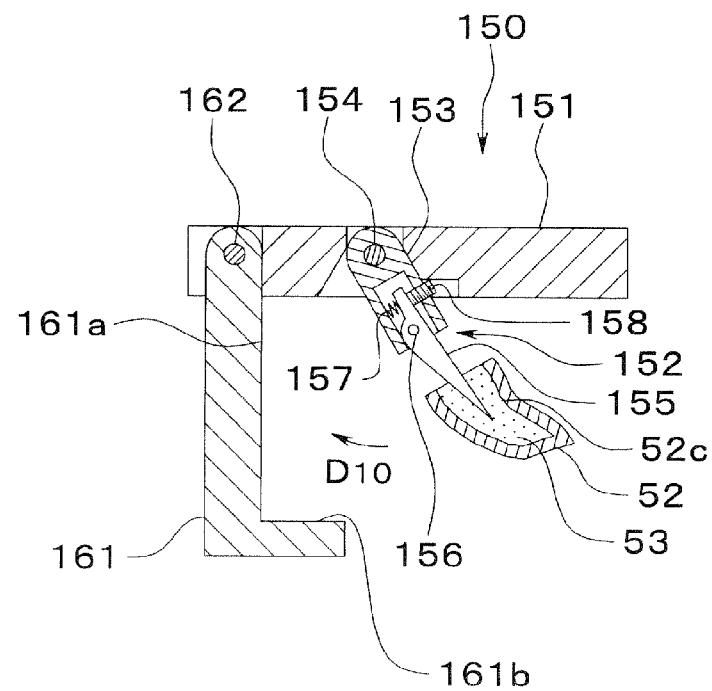
FIG. 33 is a sectional view along the optical axis in an artificial tooth mounting state (state in which reference plate is upright and abutment post is retracted) of a color measurement tool according to a ninth embodiment.
Figure 34:
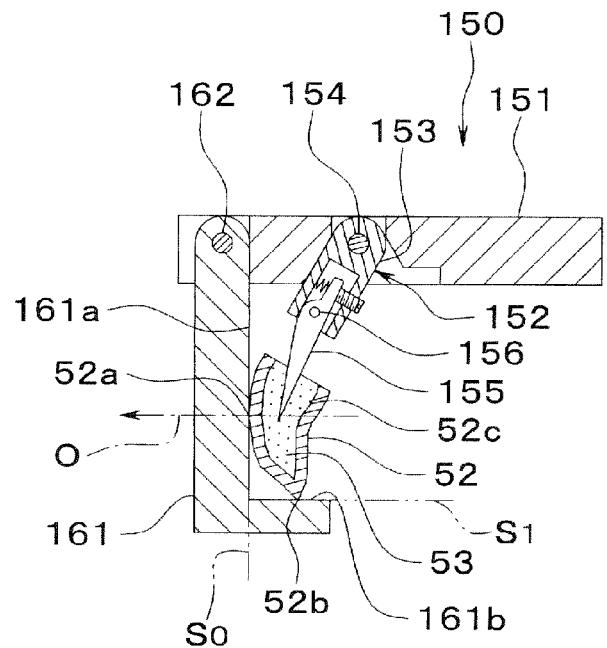
FIG. 34 is a sectional view along the optical axis in an artificial tooth positional adjustment state of the color measurement tool shown in FIG. 33.
Figure 35:
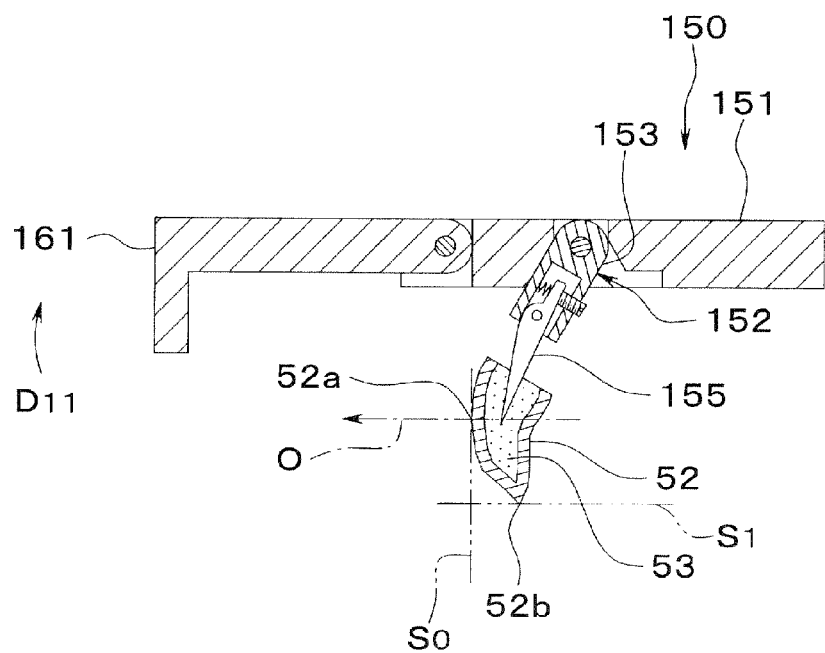
FIG. 35 is a sectional view along the optical axis in a state in which the reference plate of the color measurement tool shown in FIG. 33 has been withdrawn.

Next, a color measurement tool included in a dental color measurement tool system that is the ninth embodiment of the present invention will be described using FIGS. 33 to 35. FIG. 33 is a sectional view along the optical axis in an artificial tooth mounting state (state in which reference plate is upright and abutment post is retracted) of the color measurement tool according to the present embodiment. FIG. 34 is a sectional view along the optical axis in an artificial tooth positional adjustment state of the color measurement tool shown in FIG. 33. FIG. 35 is a sectional view along the optical axis in a state in which the reference plate of the color measurement tool shown in FIG. 33 is withdrawn.

A color measurement tool 150 of the present embodiment differs from the color measurement tool 60 of the first embodiment in that the color measurement tool 150 includes a rotatable abutment post and a rotatable reference plate. The color measurement tool 150 of the present embodiment can also be applied to a case in which an artificial tooth to be mounted has an irregular shape. The remaining configuration, that is, the abutment plate and the pair of guide posts, is the same as that provided in the color measurement tool 60, and a dark box that is the same as the dark box 65 of the first embodiment is also applied. Hereunder, only the portions that are different from the first embodiment are described.

An artificial tooth 52 that is mountable in the color measurement tool 150 of the present embodiment has a concave portion 52c that is bendingly formed as shown in FIG. 33. For example, the artificial tooth 52 is an artificial tooth with an irregular shape that is difficult to mount to the abutment post 62 of the color measurement tool 60 of the first embodiment. However, by applying the color measurement tool 150, color measurement photographing of the above described irregular shaped artificial tooth can be performed.

The abutment post 152 of the color measurement tool 150 includes a post base 153 that is rotatably supported by a support shaft 154 on the abutment plate 151, and an artificial tooth mounting portion 155 having a pointed convex portion that is supported via a support shaft 156 by the post base. By rotating the post base 153, the artificial tooth mounting portion 155 can be rotatingly moved between a rearward position (FIG. 33) on a side opposite the camera that is an artificial tooth mounting position and a frontward position (photographing position, see FIG. 34) on the camera side that is an adjustment position. In this connection, the relative position of the artificial tooth mounting portion 155 with respect to the post base 153 can be adjusted by rotating against the urging force of the spring 157 in accordance with the screw-in position of a screw member 158 arranged in the post base 153. Positional adjustment of the artificial tooth mounting portion 155 is performed according to the shape of the artificial tooth 52 to be mounted, so that the artificial tooth 52 can be retained at the appropriate position.

Further, as shown in FIGS. 33 and 35, a reference plate 161 that can be rotated from an upright position that is an adjustment position at the front (camera side) of the abutment post to a withdrawn position is supported as an artificial tooth positional adjustment member by a support shaft 162 on the abutment plate 151 of the color measurement tool 150.

The reference plate 161 is formed in an L shape, and has an optical-axis direction color measurement reference surface 161a at the inner surface of an arm portion and a Y0-direction color measurement reference surface 161b at the inner surface of an L-shaped distal end portion. When the reference plate 161 is in an upright position state (FIG. 34), the lower part of the color measurement reference surface 161a abuts against a notched groove surface of the abutment plate 151 to position the color measurement reference surface 161a on the color measurement reference plane S0 in the optical axis direction of the camera in the set state for photographing. Further, the color measurement reference surface 161b of the L-shaped distal end portion is on the same plane as the distal end surface of the convex portions (not shown) of the guide posts, and is positioned on the color measurement reference plane S1 in the vertical direction of the camera in the set state for photographing.

When mounting the artificial tooth 52 in the color measurement tool 150, as shown in FIG. 33, the reference plate 161 is placed upright and the abutment post 152 is tilted to a rearward position. In that state, similarly to the case of the color measurement tool 60, the artificial tooth 52 is inserted onto the artificial tooth mounting portion 155 of the abutment post 152 in a state in which wax 53 has been filled in the concave portion 52c.

Subsequently, as shown in FIG. 34, the abutment post 152 is rotated forward in the D10 direction to cause the front face 52a of the artificial tooth 52 to abut against the color measurement reference surface 161a of the reference plate 161. Further, the photographer performs positional adjustment so that an incisal portion 52b of the artificial tooth 52 abuts against the color measurement reference surface 161b. After completing positional adjustment of the artificial tooth 52 as described above, the reference plate 161 is rotated clockwise in the D11 direction so as to withdraw the reference plate 161 away from the front of the artificial tooth 52, as shown in FIG. 35.

The color measurement tool 150 for which positional adjustment of the artificial tooth 52 has been performed is mounted in the dark box, and similarly to the first embodiment, the color measurement tool 150 is positioned and mounted at the bite portion 31e at the distal end of the contact cap 31 to place the color measurement tool 150 in the set state for photographing. In this set state, color measurement photographing of the artificial tooth 52 is performed with the camera 2.

The same advantages as those of the first embodiment can be obtained according to the color measurement tool 150 of the present embodiment described above. In particular, in the case of the present embodiment, the artificial tooth 52 that has an irregular shape can be mounted to the artificial tooth mounting portion 155 that is supported by the abutment post 152, and color measurement photographing of the artificial tooth 52 can be performed by the color measurement tool 150. Further, it is possible to adjust the relative position of the artificial tooth mounting portion 155 with respect to the post base 153 in accordance with the shape of the concave portion 52c of the artificial tooth 52 to thereby place the artificial tooth 52 in a suitable photographing position. Moreover, with the reference plate 161 in an upright state, since positional adjustment of the artificial tooth with respect to the color measurement reference planes S0 and S1 on the camera side can be performed at the same time, the adjustment work is performed with ease.

In this connection, a configuration may also be adopted in which the U-shaped urging spring 125 of the sixth embodiment is mounted to the reference plate 161 so that the reference plate 161 is switchingly urged in two directions.

Figure 36:
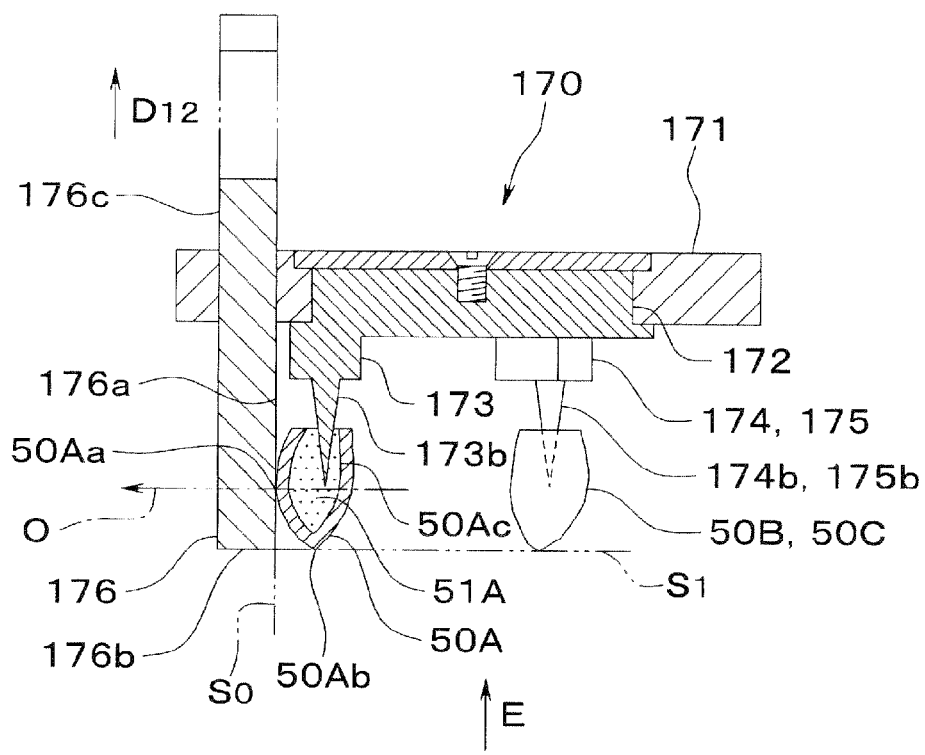
FIG. 36 is a sectional view along the optical axis that shows a state (artificial tooth positional adjustment state) in which a reference plate is positioned in front of an abutment post on a rotary index table in a color measurement tool of a tenth embodiment.
Figure 37:
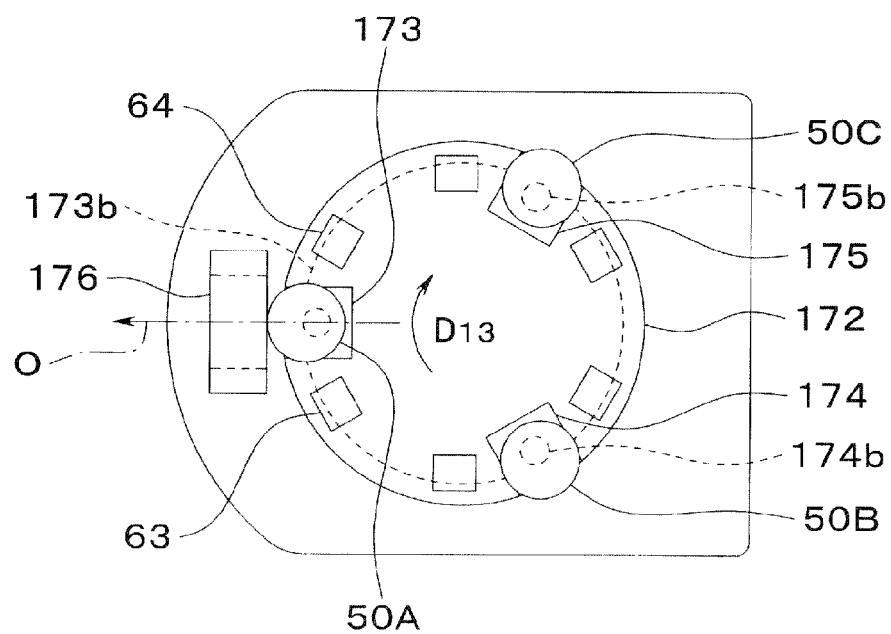
FIG. 37 is a view from the direction of arrow E in FIG. 36, and illustrates the arrangement of abutments post on a rotary index table of the aforementioned color measurement tool.
Figure 38:
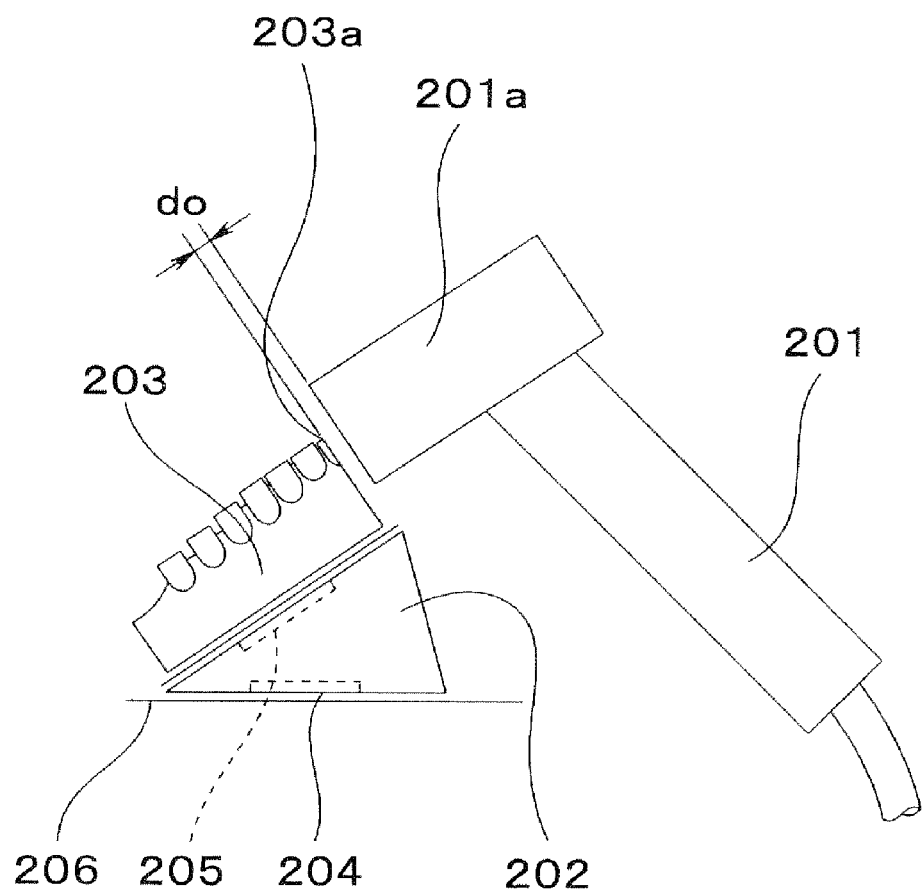
FIG. 38 is a view that illustrates a state in which color measurement (photographing) of an artificial tooth is performed using a color measuring camera, in which a conventional artificial tooth mounting stand is applied.

Next, a color measurement tool included in a dental color measurement tool system that is the tenth embodiment of the present invention will be described using FIGS. 36 and 37. FIG. 36 is a sectional view along the optical axis that shows a state (artificial tooth positional adjustment state) in which a reference plate is positioned in front of an abutment post on a rotary index table in a color measurement tool of the present embodiment. FIG. 37 is a view from the direction of arrow E in FIG. 36, and illustrates the arrangement of the abutment post on the rotary index table of the aforementioned color measurement tool.

A color measurement tool 170 of the present embodiment differs from the color measurement tool 60 of the first embodiment in that the color measurement tool 170 has a rotary index table on which a plurality of abutment posts and guide posts are arranged on an abutment plate, and includes a reference plate that is slidable in the Y0 direction (vertical direction). The pair of guide posts and the abutment post are the same as those provided in the color measurement tool 60, and a dark box that is the same as the dark box 65 of the first embodiment is also applied. Hereunder, only the portions that are different from the first embodiment are described.

Abutment posts 173, 174, and 175 and pairs of guide posts 63 and 64 that are disposed on both sides of each abutment post are arranged on a rotary index table (hereunder, referred to as "rotary table") 172 that is provided in the abutment plate 171 of the color measurement tool 170 of the present embodiment. The abutment posts 173, 174, and 175 and pairs of guide posts 63 and 64 are positioned so as to divide the rotary index table 172 into three parts. A reference plate 176 as an artificial tooth positional adjustment member that is capable of a sliding movement in the Y0 direction is arranged at the front side (camera side) of the rotary table 172.

The abutment posts 173, 174, and 175 have the same shape, and are provided with a pointed convex portion 173b, 174b, and 175b, respectively, as an artificial tooth mounting portion that is centered on the optical axis O when the respective abutment post is in a color measurement photographing state.

The guide posts 63 and 64 have the same shape as the guide posts 63 and 64 provided in the color measurement tool 60 of the first embodiment.

The reference plate 176 has a color measurement reference surface 176a in the optical axis direction and a color measurement reference surface 176b in the Y0 direction. The reference plate 176 engages with and is supported by a guide hole of the abutment plate 171 in a state in which the reference plate 176 can slide in the Y0 direction. In an adjustment position state in which the reference plate 176 has been moved downward in the Y0 direction and a stopper 176c abuts against the abutment plate 171, the color measurement reference surface 176b of the distal end is on the same plane as the distal end surface of the convex portions (not shown) of the guide posts 63 and 64 and, as shown in FIG. 36, is located on the color measurement reference plane S1 in the vertical direction of the camera 2 in the above described set state for photographing. The color measurement reference surface 176a is located on the color measurement reference plane S0 in the optical axis direction of the camera 2 in the above described set state for photographing.

Three artificial teeth 50A, 50B, and 50C are mounted in the color measurement tool 170, and positional adjustment of each tooth is performed. First, similarly to the case of the color measurement tool 60, the artificial tooth 50A is inserted onto the pointed convex portion 173b of the abutment post 173 in a state in which wax 51 has been filled in a concave portion 50Ac. Subsequently, the rotary table 172 is rotatingly driven to position the abutment post 173 on the front side (camera side) of the abutment plate 171. Then, the reference plate 176 is pushed downward as far as the adjustment position at which the stopper 176c abuts against the abutment plate 171 as described above.

In the state in which the reference plate is pushed down as described above, the photographer confirms that the front face 50Aa of the artificial tooth 50A abuts against the color measurement reference surface 176a of the reference plate 176. If the front face 50Aa of the artificial tooth 50A is separated from the color measurement reference surface 176a, the photographer causes the front face 50Aa to abut against the color measurement reference surface 176a. The photographer also positions the incisal portion 50Ab of the artificial tooth 50A at the color measurement reference surface 176b. Subsequently, the artificial teeth 50B and 50C are similarly mounted in the pointed convex portions 174b and 175b of the abutment posts 174 and 175, the rotary table 172 is rotatingly driven to be positioned at the front of the reference plate 176, and positional adjustment of each artificial tooth is performed in the same manner.

After completing positional adjustment for the artificial teeth 50A, 50B, and 50C, respectively, the reference plate 176 is slid upward in the D12 direction so as to withdraw the reference plate 176 away from the front (camera side) of the relevant artificial tooth.

The color measurement tool 170 for which positional adjustment of each artificial tooth has been performed is mounted in the dark box, and the rotary table 172 is rotatingly driven to set one of the artificial teeth 50A, 50B, and 50C at a position on the optical axis O. Then, similarly to the first embodiment, the color measurement tool 170 is positioned and mounted at the bite portion 31e at the distal end of the contact cap 31 to place the color measurement tool 170 in the set state for photographing, and color measurement photographing is performed with the camera 2. Next, the camera 2 is withdrawn, the rotary table 172 is rotatingly driven to set another artificial tooth at a position on the optical axis O, and color measurement photographing is similarly performed with the camera 2.

The same advantages as those of the first embodiment can be obtained by applying the color measurement tool system of the present embodiment described above. In particular, in the case of the present embodiment, by mounting a plurality of artificial teeth to a plurality of abutment posts arranged on the rotary table 172, color measurement photographing of the plurality of artificial teeth can be performed by mounting the color measurement tool in the dark box a single time, and thus the time required for photographing can be reduced.

In this connection, although a configuration in which a plurality of abutment posts are arranged on the rotary table 172 is adopted for the above described color measurement tool 170, it is also possible to adopt a configuration in which a plurality of abutment posts are disposed along the X0 direction on a table that is slidable in the X0 direction (horizontal direction).

The dental color measurement tool according to the present invention can be utilized as a dental color measurement tool that can stably hold an artificial tooth at a suitable position with respect to a color measurement device.

It is to be understood that the present invention is not limited to the above described embodiments, and various changes and modifications can be made thereto at the implementation stage in a range that does not depart from the spirit and scope of the invention. Further, the embodiments described above include inventions at various stages. By appropriately combining a plurality of structural requirements disclosed in the embodiments, the inventions at various stages can be also extracted.

What is claimed is:

1. A dental color measurement tool that is adapted to be disposed opposite an opening for capturing a light from an artificial tooth that is to undergo color measurement with a color measurement device, comprising:
   at least one pair of guide posts having an engaging portion corresponding to an engaging portion on the color measurement device side; and
   an abutment post that is disposed between the one pair of guide posts and has a shape that enables mounting of the artificial tooth, and which is provided with a color measurement reference surface in a direction of a color measurement light axis of the color measurement device.

2. The dental color measurement tool according to claim 1, wherein the guide posts are provided with a color measurement reference surface in a longitudinal direction of the abutment post among directions orthogonal to the color measurement light axis.

3. The dental color measurement tool according to claim 2, wherein the abutment post performs positioning of a reference plate by interfitting with the reference plate.

4. The dental color measurement tool according to claim 2, further comprising a reference plate which includes a magnetic material, and wherein magnets are disposed in the abutment post and an abutment plate, and the reference plate is positioned by the abutment post and the abutment plate by being brought in close contact by a magnetic force of the magnets disposed in the abutment post and the abutment plate.

5. The dental color measurement tool according to claim 3, wherein the reference plate is rotatably attached to an abutment plate.

6. The dental color measurement tool according to claim 5, wherein the reference plate has a rotational support portion that enables rotation with respect to the abutment plate, and the rotational support portion is formed with a hinge portion that is bi-directionally rotatable.

7. The dental color measurement tool according to claim 3, wherein the abutment post is movable in the color measurement light axis direction, and the reference plate has a color measurement reference surface in a longitudinal direction of the abutment post among directions orthogonal to the color measurement light axis of an artificial tooth.

8. The dental color measurement tool according to claim 3, wherein the abutment post is rotatably supported so that an artificial tooth mounting portion of the abutment post is moveable in the color measurement light axis direction, and the reference plate has a color measurement reference surface in the color measurement light axis direction, and a color measurement reference surface in a longitudinal direction of the abutment post among directions orthogonal to the color measurement light axis of the artificial tooth that is mounted.

9. The dental color measurement tool according to claim 3, wherein the abutment post is rotatably supported by a post base so that an artificial tooth mounting portion of the abutment post is movable in the color measurement light axis direction, and a stopper that restricts a rotational range of the abutment post is provided in the post base, and
   wherein the reference plate is provided with a color measurement reference surface in the color measurement light axis direction, and a color measurement reference surface in a longitudinal direction of the abutment post among directions orthogonal to the color measurement light axis.

10. The dental color measurement tool according to claim 2, including a plurality of units comprising the abutment post that is movable in a depth direction with respect to the one pair of guide posts and the color measurement light axis, wherein the plurality of units are disposed on a rotary plate with a rotational positioning function.

11. The dental color measurement tool according to claim 1, further comprising a detachably mountable reference plate that has a color measurement reference surface in the color measurement light axis direction.

12. The dental color measurement tool according to claim 11, wherein the reference plate further includes a color measurement reference surface in a longitudinal direction of the abutment post among directions orthogonal to the color measurement light axis.

13. The dental color measurement tool according to claim 1, further comprising a reference plate that has a color measurement reference surface in the color measurement light axis direction, and that is attached to an abutment plate in a condition in which the reference plate is moveable in a longitudinal direction of the abutment post among directions orthogonal to the color measurement light axis.

14. A dental color measurement tool system, comprising:
   the dental color measurement tool according to claim 1; and
   a dark box that houses the dental color measurement tool in order to block extraneous light when performing color measurement photographing of the artificial tooth that is mounted in the dental color measurement tool.

15. A dental color measurement system, comprising:
   the dental color measurement tool according to claim 1;
   a dark box that houses the dental color measurement tool in order to block extraneous light when performing color measurement photographing of an artificial tooth with the dental color measurement tool; and
   the color measurement device for performing color measurement of the artificial tooth that is mounted in the dental color measurement tool.

* * * * *